(12) United States Patent
Karlovsky et al.

(10) Patent No.: US 6,812,380 B2
(45) Date of Patent: Nov. 2, 2004

(54) COMPOSITIONS AND METHODS OF ZEARALENONE DETOXIFICATION

(75) Inventors: Petr Karlovsky, Goettingen (DE); Edmund H. Crane, III, Des Moines, IA (US); Jacob T. Gilliam, Norwalk, IA (US); Joyce R. Maddox, Omaha, NE (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 10/107,096

(22) Filed: Mar. 26, 2002

(65) Prior Publication Data

US 2003/0073239 A1 Apr. 17, 2003

Related U.S. Application Data

(60) Provisional application No. 60/318,747, filed on Sep. 11, 2001, and provisional application No. 60/279,098, filed on Mar. 27, 2001.

(51) Int. Cl.$^7$ .................. C12N 15/09; C12N 15/31; C12N 15/82; A01H 5/00; A01H 5/10
(52) U.S. Cl. .................. 800/279; 800/278; 800/288; 800/298; 800/295; 800/320; 800/317; 435/419; 435/468; 435/320.1; 536/23.2; 536/23.7
(58) Field of Search .................. 800/278, 279, 800/288, 320, 317, 298, 295; 536/23.7, 23.2, 24.1; 435/468, 419, 320.1

(56) References Cited

U.S. PATENT DOCUMENTS

| | | | |
|---|---|---|---|
| 5,716,820 A | | 2/1998 | Duvick et al. ............ 435/196 |
| 5,792,931 A | * | 8/1998 | Duvick et al. ............ 800/205 |
| 5,846,812 A | | 12/1998 | Duvick et al. ............ 435/267 |
| 5,962,304 A | | 10/1999 | Duvick et al. ............ 435/252.1 |
| 6,074,838 A | | 6/2000 | Duvick et al. ............ 435/29 |

FOREIGN PATENT DOCUMENTS

| | | |
|---|---|---|
| DE | 4205196 A1 | 9/1992 |
| EP | 0786945 B1 | 10/1995 |
| WO | WO 96/12414 | 5/1996 |
| WO | WO 96/20595 | 7/1996 |
| WO | WO 98/22602 | 5/1998 |

OTHER PUBLICATIONS

Lazar et al. Molecular and Cellular Biology, 1988, vol. 8, No. 3, pp. 1247–1257.*
Broun et al. Science, 1998, vol. 282, pp. 131–133.*
Zhang et al. Engineered Detoxification Confers Resistance Against a Pathogenic Bacterium. Nature Biotechnology (1999), vol. 17, pp. 1021–1024.*
Megharaj, et al., 1997, Lett. App. Microbiol., 24: 329–333, *Total biodegradation of the oestrogenic mycotoxin zearalenone by a bacterial culture.*
Karlovsky, Petr, 1999, Nat. Toxins, 7: 1–23, *Biological Detoxification of Fungal Toxins and its Use in Plant Breeding, Feed and Food Production.*
Takahashi–Ando, N., et al. "A Novel Lactonohydrolase Responsible for the Detoxification of Zearalenone: Enzyme Purification and Gene Cloning," *Biochem. J.* 2002, pp. 1–6, vol. 365.

* cited by examiner

*Primary Examiner*—Medina A. Ibrahim
(74) *Attorney, Agent, or Firm*—Alston & Bird LLP

(57) ABSTRACT

The present invention provides nucleotide sequences encoding zearalenone detoxification polypeptides, and methods for mycotoxin detoxification using the sequences. One method comprises stably incorporating into the genome of a plant cell, a nucleotide sequence of the present invention operably linked to a heterologous promoter and regenerating a stably transformed plant that expresses the nucleotide sequence.

21 Claims, No Drawings

COMPOSITIONS AND METHODS OF ZEARALENONE DETOXIFICATION

CROSS-REFERENCE TO RELATED APPLICATIONS

This application claims the benefit of U.S. Application No. 60/318,747, filed Sep. 11, 2001, and Application No. 60/279,098, filed Mar. 27, 2001, which are hereby incorporated herein in their entirety by reference.

FIELD OF THE INVENTION

The present invention relates to compositions and methods for detoxification or degradation of mycotoxins. The method has broad application in agricultural biotechnology, crop agriculture, and in the improvement of food grain quality.

BACKGROUND OF THE INVENTION

Fungal diseases are common problems in crop agriculture. Many strides have been made against plant diseases as exemplified by the use of hybrid plants, pesticides, and improved agricultural practices. However, as any grower or home gardener can attest, the problems of fungal plant disease continue to cause difficulties in plant cultivation. Thus, there is a continuing need for new methods and materials for solving the problems caused by fungal diseases of plants.

These problems can be met through a variety of approaches. For example, the infectious organisms can be controlled through the use of agents that are selectively biocidal for the pathogens. Another method is interference with the mechanism by which the pathogen invades the host crop plant. Yet another method, in the case of pathogens that cause crop loss, is interference with the mechanism by which the pathogen causes injury to the host crop plant. In the case of pathogens that produce toxins that are undesirable to mammals or other animals that feed on the crop plants, interference with toxin production, storage, or activity can be beneficial.

Within the Gibberella species are several important pathogens which attack corn and other cereal crops in various countries. In corn, Gibberella is known to cause root, stem, and ear rot that result in severe crop reduction. The etiology of Gibberella ear mold is poorly understood, although physical damage to the ear and certain environmental conditions can contribute to its occurrence (Nelson et al. (1992) *Mycopathologia* 117:29–36). Gibberella maybe isolated from most field grown maize, even when no visible mold is present. Gibberella species that infect plants produce mycotoxins that may accumulate in infected plants or in stored grains, presenting serious health consequences for livestock and humans consuming grains and grain-derived products. The potential for transmission of these mycotoxins into eggs and meat has also been demonstrated (D'Mello et al. (1999) *Anim. Feed Sci. & Tech.* 80:183–205). Gibberella infection has been associated with chronic or acute mycotoxicoses in both farm animals and man.

Certain Gibberella species produce a mycotoxin, zearalenone, a non-steroidal estrogen. Zearalenone, produced mainly by *Gibberella zeae* (anamorph *Fusarium graminearum*), occurs in Gibberella-infected corn, wheat, barley, and other cereal crops. Zearalenone has been detected in hay, feed, corn, sorghum, dairy rations and barley that caused toxicosis in livestock in various countries (Ueno et al. (1985) *CRC Critical Rev. Toxicol.* 14:99). Zearalenone causes reproductive disorders in farm animals thereby compromising livestock health and productivity (Vanyi et al. (1995) *Maygar Allatorvosok Lapja* 50:424–430; Diekman & Green (1992) *J. Anim. Sci.* 50:1615–1627; Dacasto et al. (1995) *Vet. Hum. Toxicol.* 37:359–361; Etienne & Dourmad (1994) *Livestock Production Science* 40:99–113). For example, when consumed by swine, zearalenone may incite a hyperestrogenic response, including infertility, edematous swelling and reddening of the vuvla, reduced litter size, weak piglets, and congenital lesions of the external genitalia in piglets (Dacasto et al. (1995) *Vet. Hum. Toxicol.* 37:359–361; Chang et al. (1979) *Am. J. Vet. Res.* 40:1260–1267). It is also physiologically active in cattle, rats, mice, guinea pigs, poultry, and plants (U.S. Pat. Nos. 5,962,304 and 6,074,838). Zearalenone has been shown to be teratogenic in rats (Ueno et al. (1976) *Cancer Res.* 36:445; Ueno et al. (1978) *Cancer Res.* 38:536), and to induce modulation of uterine tissues in mice (Ueno et al. (1970) *Jap. J. Exp. Med.* 45:199).

Among farm animals, pigs and sheep are most sensitive to dietary zearalenone. However, reproductive distortions due to consumption of zearalenone-contaminated feedstuff have been described in other animals including cattle (Coppock et al. (1990) *Vet. Hum. Toxicol.* 32:246–248) and mink (Bursian et al. (1992) *J. Appl. Toxicol.* 12:85–90). These citations are herein incorporated by reference.

Zearalenone has also been detected in commercially available cereal-based foods including baby foods and beer (Schollenberger et al. (1999) *Mycopathologia* 147:49–57 and Zollner et al. (2000) *J Chromatogr B Biomed Sci Appl.* 738:233–241). Zearalenone and/or its derivatives are genotoxic (Pfohl-Leszkowicz et al. (1995) *Carcinogenesis* 16:2315–2320), carcinogenic in mice (Grosse et al. (1997) *Cancer Lett.* 114:225–229; Battershill et al. (1998) *Hum. Exp. Toxicol.* 17:193–205), and induce hepatic carcinomas in the Armenian hamster (Coe, et al. (1992) *Proc. Natl. Acad. Sci.* 89:1085–1089). In humans, zearalenone exhibits estrogenic effects (Pitt (2000) *Br. Med. Bull.* 56:184–192), causes hyperestrogenic syndrome, particularly in children (Szuets et al. (1997) *5th European Fusarium Seminar, Proceedings*:429–436), and at low concentrations, stimulates human breast cancer cells to enter the cell cycle (Dees et al. (1997) *Environ Health Perspect* 105:633–636). Each reference is herein incorporated by reference Accordingly, there is a need in the art for novel methods with which zearalenone may be eliminated from a plant or harvested grain.

SUMMARY OF THE INVENTION

The present invention provides compositions and methods for the detoxification of zearalenone and structurally related mycotoxins. In particular, the present invention provides nucleotide sequences encoding zearalenone esterase polypeptides. More specifically, the present invention provides the nucleotide sequences ZES1 (SEQ ID NO:1), ZES2 (SEQ ID NO:3), ZES2b (SEQ ID NO:5) or biologically active variants thereof. Also provided are amino acid sequences (SEQ ID NOS:2,4, 6 and 7) and biologically active variants thereof encoded by the ZES1, ZES2 and ZES2b nucleotide sequences of the invention. The amino acid sequence set forth in SEQ ID NO:6 and 7 is the predicted amino acid sequence for ZES2b Further compositions of the invention include expression cassettes and vectors for the expression of the sequences in plants and other organisms. Transformed plants, plant tissues, and seed, as well as, other transformed host cells are provided.

The invention further provides a method for detoxification of a mycotoxin in a plant. The method comprises stably incorporating into the genome of a plant a nucleotide sequence encoding a polypeptide of the invention operably linked to a promoter active in the plant. Another aspect of the invention provides a method for detoxification of a mycotoxin in or on a plant, grain or processed grain, by applying a microorganism having stably incorporated a heterologous nucleotide sequence of the invention. Additionally, the present invention provides a method for detoxification of mycotoxins in plants, grains or processed grains intended for use in feed or food. The method comprises applying to plants or grains a composition comprising a ZES1, ZES2, or ZES2b polypeptide or biologically active variant thereof.

The invention further provides a method for expression of a mycotoxin-degrading polypeptide in a non-human animal cell or population of non-human animal cells. The method comprises stably incorporating into the genome of a non-human animal cell a nucleotide sequence encoding a polypeptide of the invention operably linked to a promoter active in the non-human animal cell. The transformed cells are then cultured using appropriate methods. The expression of a polypeptide having the ability to degrade a mycotoxin such as zearalenone and the structural analogs thereof may occur in vitro or in vivo. The non-human animal cells include, but are not limited to, animal cells of any non-human origin, including but not limited to, mammals such as swine, sheep, goats, mink, cattle, horses, canines, and rodents. In an embodiment of the invention, the polypeptide is preferentially expressed in digestive tract cells including, but not limited to, salivary gland cells, liver cells, and gall bladder cells. The expressed polypeptide may be secreted from the non-human animal cell in which it is expressed. Secretion of the polypeptide may be improved or altered by operably linking a mammalian secretory signal to a nucleotide sequence of the invention.

DETAILED DESCRIPTION OF THE INVENTION

The present invention provides methods and compositions for the detoxification of mycotoxins, particularly zearalenone and structurally related molecule. Compositions of the present invention include nucleic acid molecules comprising novel nucleotide sequences encoding polypeptides that are involved in detoxifying zearalenone. More particularly, compositions of the present invention comprise coding regions isolated from the fungus *Gliocladium roseum*, the ZES1 and ZES2 nucleotide sequences that encode zearalenone detoxification proteins. In particular, the present invention provides for isolated nucleic acid molecules comprising nucleotide sequences encoding the amino acid sequences shown in SEQ ID NOS:2, 4, 6, and 7. Further provided are polypeptides having an amino acid sequence encoded by the nucleic acid molecules described herein, for example those set forth in SEQ ID NOS:1, 3, and 5 and fragments and variants thereof.

As discussed elsewhere herein, the ZES1, ZES2, ZES2b sequences of the invention have sequence similarity to known esterases and are upregulated in the presence of the zearalenone mycotoxin. Hence the sequences of the invention may find use in the detoxification of mycotoxins. A mycotoxin includes any poisonous or toxic molecule produced by a fungus. Many mycotoxins are esters, including brefeldin A, fumonisin, aflatoxins, ochratoxins, and zearalenone. By "detoxifying mycotoxins", "mycotoxin detoxification," or "having the ability to detoxify mycotoxins" is meant any modification to a mycotoxin that causes a decrease or loss in its toxic activity. Such a change comprises cleavage of any of the various bonds, oxidation, reduction, the addition or deletion of a chemical moiety, or any other change that affects the activity of the molecule. Hence polypeptides having mycotoxin detoxification activity are characterized by the ability to accelerate the chemical modification of a mycotoxin molecule that causes a decrease or loss in the toxic activity of the mycotoxin. Such a change comprises cleavage of any of the various bonds, oxidation, reduction, the addition or deletion of a chemical moiety, or any other change that affects the activity of the molecule. Of particular interest in the methods of the invention is the detoxification of the mycotoxin zearalenone or structurally related mycotoxins.

By "structurally related mycotoxin" is meant any mycotoxin having a chemical structure related to a zearalenone and zearalenone analogs, as well as other mycotoxins having similar chemical structures that would be expected to be detoxified by the activity of the zearalenone degradative enzymes particularly those elaborated by *Rhodococcus globerulus, Rhodococcus erythropolis, Nocardia globerula*, or the bacteria deposited under American Type Culture Collection Accession Nos:55856, 55853, 55852, and 55851. Zearalenone derivatives include α-zearalenol, β-zearalenol, zearalanone, α-zearalanol, and β-zearalanol. Additional structurally related analogs are macrocyclic lactones, such as curvularins and dehydrocurvularins. Assays are available that would allow one of skill in the art to determine if a structurally related analog is detoxified by a polypeptide of the invention (Kneusel et al. (1994) *J. Biol. Chem.* 269:3449–3456; toxicity (Lemke et al. (1999) *J. Toxicol Environ Health.* 56:283–295; Megharaj et al. (1997) *Lett. Appl. Micro.* 24:329–333; and U.S. Pat. Nos. 5,962,304 and 6,074,838).

By "detoxifying zearalenone," "zearalenone detoxification," "having the ability to detoxify zearalenone," or "zearalenone detoxifying activity" is meant any modification to the zearalenone molecule, structurally related analog, or structurally related mycotoxin that causes a decrease or loss in its toxic activity. Such a change comprises cleavage of any of the various bonds, oxidation, reduction, the addition or deletion of a chemical moiety, or any other change that affects the activity of the molecule. While the present invention is not bound by any specific mechanism for the detoxification of the mycotoxin, the sequences of the invention may detoxify zearalenone by the cleavage of the ester linkage in the molecule, more specifically hydrolysis of the lactone bond in the molecule. By "zearalenone esterase" is meant any enzyme capable of breaking the ester linkage in zearalenone.

The invention encompasses isolated or substantially purified nucleic acid or protein compositions. An "isolated" or "purified" nucleic acid molecule or protein, or biologically active portion thereof, is substantially or essentially free from components that normally accompany or interact with the nucleic acid molecule or protein as found in its naturally occurring environment. Thus, an isolated or purified nucleic acid molecule or protein is substantially free of other cellular material, or culture medium when produced by recombinant techniques, or substantially free of chemical precursors or other chemicals when chemically synthesized. Preferably, an "isolated" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, preferably culture medium represents less than about 30%, 20%, 10%, 5%, or 1% (by dry weight) of chemical precursors or non-protein-of-interest chemicals.

Fragments and variants of the disclosed nucleotide sequences and polypeptides encoded thereby are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence detoxify mycotoxins. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of the ZES1, ZES2, or ZES2b nucleotide sequences that encodes a biologically active portion of a zearalenone detoxifying protein of the invention will encode at least 15, 25, 30, 50, 100, 150, 200, 250 or 260 contiguous amino acids, or up to the total number of amino acids present in a full-length zearalenone esterase protein of the invention (for example, 268, 262, 264 and 264 amino acids for SEQ ID NOS:2, 4, 6, and 7 respectively). Fragments of a ZES1, ZES2 or ZES2b nucleotide sequence that are useful as hybridization probes or PCR primers generally need not encode a biologically active portion of a zearalenone detoxifying protein.

Thus, a fragment of a ZES1, ZES2, or ZES2b nucleotide sequence may encode a biologically active portion of a zearalenone detoxifying polypeptide, or it may be a fragment that can be used as a hybridization probe or PCR primer using methods disclosed below. A biologically active portion of a zearalenone detoxifying polypeptide can be prepared by isolating a portion of one of the zearalenone esterase nucleotide sequences of the invention, expressing the encoded portion of the zearalenone detoxifying polypeptide (e.g., by recombinant expression in vitro), and assessing the activity of the encoded portion of the zearalenone detoxifying polypeptide. ZES polypeptides are polypeptides having at least 80%, 85%, 90%, 91%, 92%, 93%, 94%, 95%, 96%, 97%, 98%, 99%, or up to 100% identity with the polypeptide sequences of the invention and retaining biological activity. Nucleic acid molecules that are fragments of a ZES1, ZES2, or ZES2b nucleotide sequence comprise at least 16, 20, 50, 75, 100, 150, 200, 250, 300, 350, 400, 450, 500, 550, 600, 650, 700, 750 nucleotides, or up to the number of nucleotides present in full-length ZES1 or ZES2 nucleotide sequences disclosed herein (for example, 807, 789, and 795 nucleotides for SEQ ID NOS:1, 3, and 5).

By "variants" is intended substantially similar sequences. For nucleotide sequences, conservative variants include those sequences that, because of the degeneracy of the genetic code, encode the amino acid sequence of one of the zearalenone esterase polypeptides of the invention. Naturally occurring allelic variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis but which still encode a zearalenone esterase protein of the invention. Variants of a particular nucleotide sequence of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to that particular nucleotide sequence as determined by sequence alignment programs described elsewhere herein using default parameters.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Variant proteins encompassed by the present invention are biologically active, that is they continue to possess the desired biological activity of the native protein, that is, mycotoxin detoxification activity as described herein. Such variants may result from, for example, genetic polymorphism or from human manipulation. Biologically active variants of a native zearalenone detoxifying polypeptide of the invention will have at least about 40%, 50%, 60%, 65%, 70%, generally at least about 75%, 80%, 85%, preferably at least about 90%, 91%, 92%, 93%, 94%, 95%, 96%, 97%, and more preferably at least about 98%, 99% or more sequence identity to the amino acid sequence for the native protein as determined by sequence alignment programs described elsewhere herein using default parameters. A biologically active variant of a protein of the invention may differ from that protein by as few as 1–15 amino acid residues, as few as 1–10, such as 6–10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants of the ZES1, ZES2, and ZES2b polypeptides can be prepared by mutations in the DNA. Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be preferable.

Thus, the nucleotide sequences of the invention include both the naturally occurring sequences as well as mutant forms. Likewise, the proteins of the invention encompass both naturally occurring proteins as well as variations and modified forms thereof. Such variants will continue to possess the desired zearalenone esterase activity. Obviously, the mutations that will be made in the DNA encoding the variant must not place the sequence out of reading frame and preferably will not create complementary regions that could produce secondary mRNA structure. See EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays as described herein.

Variant nucleotide sequences and proteins also encompass sequences and proteins derived from a mutagenic and recombinogenic procedure such as DNA shuffling. With such a procedure, one or more different ZES coding sequences can be manipulated to create a new zearalenone esterase possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a ZES1, ZES2, or ZES2b gene of the invention and other known esterase genes to obtain a new gene coding for a protein with an improved property of interest, such as an increased $K_m$ in the case of an enzyme. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech*. 15:436–438; Moore et al. (1997) *J. Mol. Biol*. 272:336–347; Zhang et al. (1997) *Proc. Natl. Acad. Sci. USA* 94:4504–4509; Crameri et al. (1998) *Nature* 391:288–291; and U.S. Pat. Nos. 5,605,793 and 5,837,458.

The nucleotide sequences of the invention can be used to isolate corresponding sequences from other organisms, particularly other fungi, more particularly other zearalenone detoxifying microorganisms. In this manner, methods such as PCR, hybridization, and the like can be used to identify such sequences based on their sequence homology to the sequences set forth herein. Sequences isolated based on their sequence identity to the entire ZES1, ZES2, or ZES2b sequences set forth herein or to fragments thereof are encompassed by the present invention. Such sequences include sequences that are orthologs of the disclosed sequences. By “orthologs” is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

In a PCR approach, oligonucleotide primers can be designed for use in PCR reactions to amplify corresponding DNA sequences from cDNA or genomic DNA extracted from any microorganism of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the ZES1, ZES2, and ZES2b sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, the entire ZES1, ZES2 or ZES2b sequences disclosed herein, or one or more portions thereof, may be used as a probe capable of specifically hybridizing to corresponding ZES1, ZES2, or ZES2b sequences and messenger RNAs. To achieve specific hybridization under a variety of conditions, such probes include sequences that are unique among ZES sequences and are preferably at least about 10 nucleotides in length, and most preferably at least about 20 nucleotides in length. Such probes may be used to amplify corresponding ZES1, ZES2, and ZES2b sequences from a chosen microorganism by PCR. This technique may be used to isolate additional coding sequences from a desired microorganism or as a diagnostic assay to determine the presence of coding sequences in a plant or organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By “stringent conditions” or “stringent hybridization conditions” is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) Anal. Biochem. 138:267–284: $T_m$=81.5° C.+16.6 (log M)+0.41 (%GC)–0.61 (% form)–500/L; where M is the molarity of monovalent cations, %GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, N.Y.); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

Thus, isolated sequences that encode a zearalenone esterase protein and which hybridize under stringent conditions to the ZES1, ZES2, or ZES2b sequences disclosed herein, or to fragments thereof, are encompassed by the present invention.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the search-for-similarity-method of Pearson and Lipman (1988) *Proc. Natl. Acad. Sci.* 85:2444–2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (1988) *Gene* 73:237–244 (1988); Higgins et al. (1989) *CABIOS* 5:151–153; Carpet et al. (1988) *Nucleic Acids Res.* 16:10881–90; Huang et al. (1992) *CABIOS* 8:155–65; and Pearson at al. (1994) *Meth. Mol. Biol.* 24:307–331. The ALIGN program is based on the algorithm of Myers and Miller (1988) supra. A PAM120 weight residue table, a gap length penalty or 12, and a gap penalty of 4 can he used with the ALIGN program when comparing amino acid sequences. The BLAST programs a Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul et al. (1997) *Nucleic Acids Res.* 25:3389. Alternatively. PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See nebi.nlm.nih.gov (a "www" prefix must be used). Alignment may also be performed manually by inspection.

Unless otherwise stated, sequence identity/similarity values provided herein refer to the value obtained using GAP version 10 using the following parameters: % identity using GAP Weight of 50 and Length Weight of 3; % similarity using Gap Weight of 12 and Length Weight of 4, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch (1970) *J. Mol. Biol.* 48:443–453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff and Henikoff (1989) *Proc. Natl. Acad. Sci. USA* 89:10915).

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to, proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, more preferably at least 70%, 80%, 90%, and most preferably at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70% sequence identity to a reference sequence, preferably 80%, more preferably 85%, most preferably at least 90% or 95% sequence identity to the reference sequence over a specified comparison window. Preferably, optimal alignment is conducted using the homology alignment algorithm of Needleman and Wunsch (1970) *J. Mol. Biol.* 48:443–453. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The nucleic acid sequences of the present invention can be expressed in a host cell such as a microbe, insect, mammalian, or plant cells. By "microbe" is intended any microorganism (including both eukaryotic and prokaryotic microorganisms), such as fungi, yeast, bacteria, actinomycetes, algae, viruses and protozoa, as well as other unicellular structures. It is expected that those of skill in the art are knowledgeable in the numerous expression systems available for expression of a nucleic acid encoding a polypeptide of the present invention. No attempt to describe in detail the various methods known for the expression of proteins in prokaryotes or eukaryotes will be made.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous nucleotide sequence can be from a species different from that from which the nucleotide sequence was derived, or, if from the same species, the promoter is not naturally found operably linked to the nucleotide sequence. A heterologous protein may originate from a foreign species, or, if from the same species, is substantially modified from its original form by deliberate human intervention.

By "host cell" is meant a cell, which comprises a heterologous nucleic acid sequence of the invention. Host cells may be from any organism, including, for example, *E.coli, Pichia pastoris, G. roseum*, or plants. Plant host cells can be either monocotyledonous or dicotyledonous plant cells. A particularly preferred monocotyledonous host cell is a maize host cell.

The coding sequences of the invention are provided in expression cassettes for expression in the organism or host cell of interest. The cassette will include 5' and 3' regulatory sequences operably linked to a nucleotide sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The expression cassette can be incorporated into a plasmid, chromsome, mitochondrial DNA, plastid DNA, virus, or nucleic acid fragment. The cassette may additionally contain at least one additional gene to be cotransformed into the organism. Alternatively, the additional gene(s) can be provided on multiple expression cassettes.

Such an expression cassette is provided with a plurality of restriction sites for insertion of the coding sequence to be under the transcriptional regulation of the regulatory regions. The expression cassette may additionally contain selectable marker genes.

The expression cassette will include in the 5'-3' direction of transcription, a transcriptional and translational initiation region, a nucleotide sequence of the invention, and a transcriptional and translational termination region functional in plants or in the desired organism. The transcriptional initiation region, the promoter, may be native or analogous or foreign to the plant host or other type of host. Additionally, the promoter may be the natural sequence or alternatively a synthetic sequence. By "foreign" is intended that the transcriptional initiation region is not found in the native plant or host organism into which the transcriptional initiation region is introduced. As used herein, a chimeric gene comprises a coding sequence operably linked to a transcription initiation region that is heterologous to the coding sequence.

While it may be preferable to express the sequences using heterologous promoters, the promoter sequences used to regulate expression of the nucleotide sequences of the invention may be used. Such constructs would change expression levels of zearalenone esterase in *G. roseum* or other host cell of interest. Thus, the phenotype of the *G. roseum* cell or the host cell (i.e. plant, plant cell, or organism of interest) is altered.

The termination region may be native with the transcriptional initiation region, may be native with the operably linked DNA sequence of interest, or may be derived from another source. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acid Res.* 15:9627–9639.

Where appropriate, the gene(s) may be optimized for increased expression in the transformed organism. That is, the nucleotide sequences can be synthesized using codons that allow preferred expression in the organism of interest and thereby allow improved expression. See, for example, Campbell and Gowri (1990) *Plant Physiol.* 92:1–11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picomavirus leaders, for example, EMCV leader (Encephalomyocarditis 5' noncoding region) (Elroy-Stein et al. (1989) *Proc. Natl. Acad. Sci. USA* 86:6126–6130); potyvirus leaders, for example, TEV leader (Tobacco Etch Virus) (Gallie et al. (1995) *Gene* 165(2):233–238), MDMV leader (Maize Dwarf Mosaic Virus) (*Virology* 154:9–20), and human immunoglobulin heavy-chain binding protein (BiP) (Macejak et al. (1991) *Nature* 353:90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) in *Molecular Biology of RNA*, ed. Cech (Liss, N.Y.), pp. 237–256); and maize chlorotic mottle virus leader (MCMV)

(Lommel et al. (1991) *Virology* 81:382–385). See also, Della-Cioppa et al. (1987) *Plant Physiol*. 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4 dichlorophenoxyacetate (2,4-D). See generally, Yarranton (1992) *Curr. Opin. Biotech*. 3:506–511; Christopherson et al. (1992) *Proc. Natl. Acad. Sci. USA* 89:6314–6318; Yao et al. (1992) *Cell* 71:63–72; Reznikoff(1992) *Mol. Microbiol*. 6:2419–2422; Barkley et al. (1980) in *The Operon*, pp. 177–220; Hu et al. (1987) *Cell* 48:555–566; Brown et al. (1987) *Cell* 49:603–612; Figge et al. (1988) *Cell* 52:713–722; Deuschle et al. (1989) *Proc. Natl. Acad. Sci. USA* 86:5400–5404; Fuerst et al. (1989) *Proc. Natl. Acad. Sci. USA* 86:2549–2553; Deuschle et al. (1990) *Science* 248:480–483; Gossen (1993) Ph.D. Thesis, University of Heidelberg; Reines et al. (1993) *Proc. Natl. Acad. Sci. USA* 90:1917–1921; Labow et al. (1990) *Mol. Cell. Biol*. 10:3343–3356; Zambretti et al. (1992) *Proc. Natl. Acad. Sci. USA* 89:3952–3956; Baim et al. (1991) *Proc. Natl. Acad. Sci. USA* 88:5072–5076; Wyborski et al. (1991) *Nucleic Acids Res*. 19:4647–4653; Hillenand-Wissman (1989) *Topics Mol. Struc. Biol*. 10:143–162; Degenkolb et al. (1991) *Antimicrob. Agents Chemother*. 35:1591–1595; Kleinschnidt et al. (1988) *Biochemistry* 27:1094–1104; Bonin (1993) Ph.D. Thesis, University of Heidelberg; Gossen et al. (1992) *Proc. Natl . Acad. Sci. USA* 89:5547–5551; Oliva et al. (1992) *Antimicrob. Agents Chemother*. 36:913–919; Hlavka et al. (1985) *Handbook of Experimental Pharmacology*, Vol. 78 (Springer-Verlag, Berlin); Gill et al. (1988) *Nature* 334:721–724. In addition, a DNA construct may contain selectable marker genes appropriate for non-plant host cells, for example, *E. coli* cells. Such disclosures are herein incorporated by reference. The above list of selectable marker genes is not meant to be limiting. Any selectable marker gene can be used in the present invention.

As used herein, "promoter" includes reference to a region of DNA upstream from the start of transcription and involved in recognition and binding of RNA polymerase and other proteins to initiate transcription. A "plant promoter" is a promoter capable of initiating transcription in plant cells. Exemplary plant promoters include, but are not limited to, those that are obtained from plants, plant viruses, and bacteria that comprise genes expressed in plant cells, such as Agrobacterium or Rhizobium. Examples are promoters that preferentially initiate transcription in certain tissues, such as leaves, roots, seeds, fibers, xylem vessels, tracheids, or sclerenchyma. Such promoters are referred to as "tissue preferred". A "cell type" specific promoter primarily drives expression in certain cell types in one or more organs, for example, vascular cells in roots or leaves. An "inducible" promoter is a promoter that is under environmental control. Examples of environmental conditions that may effect transcription by inducible promoters include anaerobic conditions or the presence of light. Another type of promoter is a developmentally regulated promoter, for example, a promoter that drives expression during pollen development. Tissue-preferred, cell type specific, developmentally regulated, and inducible promoters constitute the class of "non-constitutive" promoters. A "constitutive" promoter is a promoter that is active under most environmental conditions.

Such constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810–812); rice actin (McElroy et al. (1990) *Plant Cell* 2:163–171); ubiquitin (Christensen et al. (1989) *Plant Mol. Biol*. 12:619–632 and Christensen et al. (1992) *Plant Mol. Biol*. 18:675–689); pEMU (Last et al. (1991) *Theor. Appl. Genet*. 81:581–588); MAS (Velten et al. (1984) *EMBO J*. 3:2723–2730); ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; and 5,608,142.

Generally, it will be beneficial to express the gene from an inducible promoter, particularly from a pathogen-inducible promoter. Such promoters include those from pathogenesis-related proteins (PR proteins), which are induced following infection by a pathogen; e.g., PR proteins, SAR proteins, beta-1,3-glucanase, chitinase, etc. See, for example, Redolfi et al. (1983) *Neth. J. Plant Pathol*. 89:245–254; Uknes et al. (1992) *Plant Cell* 4:645–656; and Van Loon (1985) *Plant Mol. Virol*. 4:111–116. See also the copending application entitled "Inducible Maize Promoters," U.S. application Ser. No. 09/257,583, filed Feb. 25, 1999, herein incorporated by reference.

Of interest are promoters that are expressed locally at or near the site of pathogen infection. See, for example, Marineau et al. (1987) *Plant Mol. Biol*. 9:335–342; Matton et al. (1989) *Molecular Plant-Microbe Interactions* 2:325–331; Somsisch et al. (1986) *Proc. Natl. Acad. Sci. USA* 83:2427–2430; Somsisch et al. (1988) *Mol. Gen. Genet*. 2:93–98; and Yang (1996) *Proc. Natl. Acad. Sci. USA* 93:14972–14977. See also, Chen et al. (1996) *Plant J*. 10:955–966; Zhang et al. (1994) *Proc. Natl. Acad. Sci. USA* 91:2507–2511; Warner et al. (1993) *Plant J*. 3:191–201; Siebertz et al. (1989) *Plant Cell* 1:961–968; U.S. Pat. No. 5,750,386 (nematode-inducible); and the references cited therein. Of particular interest is the inducible promoter for the maize PRms gene, whose expression is induced by the pathogen *Fusarium moniliforme* (see, for example, Cordero et al. (1992) *Physiol. Mol. Plant Path*. 41:189–200).

Chemical-regulated promoters can be used to modulate the expression of a gene in a plant through the application of an exogenous chemical regulator. Depending upon the objective, the promoter may be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena et al. (1991) *Proc. Natl. Acad. Sci. USA* 88:10421–10425 and McNellis et al. (1998) *Plant J.* 14(2):247–257) and tetracycline-inducible and tetracycline-repressible promoters (see, for example, Gatz et al. (1991) *Mol. Gen. Genet.* 227:229–237, and U.S. Pat. Nos. 5,814,618 and 5,789,156), herein incorporated by reference.

Tissue-preferred promoters can be utilized to target enhanced expression of mycotoxin detoxification polypeptides within a particular plant tissue. Tissue-preferred promoters include Yamamoto et al. (1997) *Plant J.* 12(2) 255–265; Kawamata et al. (1997) *Plant Cell Physiol.* 38(7): 792–803; Hansen et al. (1997) *Mol. Gen Genet.* 254(3): 337–343; Russell et al. (1997) *Transgenic Res.* 6(2): 157–168; Rinehart et al. (1996) *Plant Physiol.* 112(3): 1331–1341; Van Camp et al. (1996) *Plant Physiol.* 112(2): 525–535; Canevascini et al. (1996) *Plant Physiol.* 112(2): 513–524; Yamamoto et al. (1994) *Plant Cell Physiol.* 35(5): 773–778; Lam (1994) *Results Probl. Cell Differ.* 20:181–196; Orozco et al. (1993) *Plant Mol Biol.* 23(6): 1129–1138; Matsuoka et al. (1993) *Proc Natl. Acad. Sci. USA* 90(20):9586–9590; and Guevara-Garcia et al. (1993) *Plant J.* 4(3):495–505. Such promoters can be modified, if necessary, for weak expression.

"Seed-preferred" promoters include both "seed-specific" promoters (those promoters active during seed development such as promoters of seed storage proteins) as well as "seed-germinating" promoters (those promoters active during seed germination). See Thompson et al. (1989) *BioEssays* 10:108, herein incorporated by reference. Such seed-preferred promoters include, but are not limited to, Cim1 (cytokinin-induced message); cZ19B1 (maize 19 kDa zein); milps (myo-inositol-1-phosphate synthase); and ce1A (cellulose synthase) (see the copending application entitled "Seed-Preferred Promoters," U.S. application Ser. No. 09/377,648, filed Aug. 19, 1999, herein incorporated by reference). Gama-zein is a preferred endosperm-specific promoter. Glob-1 is a preferred embryo-specific promoter. For dicots, seed-specific promoters include, but are not limited to, bean β-phaseolin, napin, β-conglycinin, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc.

The methods of the invention involve introducing a nucleotide construct into a plant or other host organism. By "introducing" is intended presenting to the host organism the nucleotide construct in such a manner that the construct gains access to the interior of a cell of the host. The methods of the invention do not depend on a particular method for introducing a nucleotide construct to a host, only that the nucleotide construct gains access to the interior of at least one cell of the host. The method of transformation/transfection is not critical to the instant invention; various methods of transformation or transfection are currently available. As newer methods are available to transform crops or other host cells they may be directly applied. Accordingly, a wide variety of methods have been developed to insert a DNA sequence into the genome of a host cell to obtain the transcription and/or translation of the sequence to effect phenotypic changes in the organism. Thus, any method, which provides for effective transformation/transfection of an organism or cell of interest may be employed.

Methods for introducing nucleotide constructs into plants are known in the art including, but not limited to, stable transformation methods, transient transformation methods, and virus-mediated methods. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, Agrobacterium-mediated transformation (Townsend et al., U.S. Pat. No. 5,563,055; Zhao et al., U.S. Pat. No. 5,981,840), direct gene transfer (Paszkowski et al. (1984) *EMBO J.* 3:2717–2722), and ballistic particle acceleration (see, for example, Sanford et al., U.S. Pat. No. 4,945,050; Tomes et al., U.S. Pat. No. 5,879,918; Tomes et al., U.S. Pat. No. 5,886,244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440–444 (maize); Fromm et al. (1990) *Biotechnology* 8:833–839 (maize); Hooykaas-Van Slogteren et al. (1984) *Nature* (*London*) 311:763–764; Bowen et al., U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, N.Y.), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407–413 (rice); Osjoda et al. (1996) *Nature Biotechnology* 14:745–750 (maize via *Agrobacterium tumefaciens*); all of which are herein incorporated by reference.

By "stable transformation" of a plant is intended that the nucleotide construct introduced into a plant integrates into the genome of the plant and is capable of being inherited by progeny thereof. By "transient transformation" of a plant is intended that a nucleotide construct introduced into a plant does not integrate into the genome of the plant.

The nucleotide constructs of the invention may be introduced into plants by contacting plants with a virus or viral nucleic acids. Generally, such methods involve incorporating a nucleotide construct of the invention within a viral DNA or RNA molecule. It is recognized that a zearalenone detoxifying polypeptide of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367 and 5,316,931; herein incorporated by reference.

The cells that have been transformed may be grown into plants in accordance with conventional ways. See, for example, McCormick et al. (1986) Plant Cell Reports 5:81–84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved.

The present invention may be used for transformation of any plant species, including, but not limited to, monocotyledons and dicotyledons. Examples of plant species of interest include, but are not limited to, grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, Brassica, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Examples of plant species of interest include, but are not limited to, corn (*Zea mays*), Brassica sp. (e.g., *B. napus, B. rapa, B. juncea*), particularly those Brassica species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea spp.*), coconut (*Cocos nucifera*), pineapple (*Ananas comosus*), citrus trees (*Citrus spp.*), cocoa (*Theobroma cacao*), tea (*Camellia sinensis*), banana (*Musa spp.*), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (Saccharum spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus spp.*), and members of the genus Cucumis such as cucumber (*C. sativus*), cantaloupe (*C. cantalupensis*), and musk melon (*C. melo*).

Preferably, plants of the present invention are crop plants (for example, corn, alfalfa, sunflower, Brassica, soybean, cotton, safflower, peanut, sorghum, wheat, millet, tobacco, etc.), more preferably corn and soybean plants, yet more preferably corn plants.

Plant signal sequences, including, but not limited to, signal-peptide encoding DNA/RNA sequences which target proteins to the extracellular matrix of the plant cell (Dratewka-Kos et al., (1989) *J. Biol. Chem.* 264:4896–4900), the *Nicotiana plumbaginifolia* extension gene (DeLoose et al. (1991) *Gene* 99:95–100), signal peptides which target proteins to the vacuole like the sweet potato sporamin gene (Matsuka et al. (1991) *PNAS* 88:834) and the barley lectin gene (Wilkins et al. (1990) *Plant Cell* 2:301–313), signal peptides which cause proteins to be secreted such as that of PRIb (Lind et al. (1992) *Plant Mol. Biol.* 18:47–53), or the barley alpha amylase (BAA) (Rahmatullah et al. (1989) *Plant Mol. Biol.* 12:119) and hereby incorporated by reference, or signal peptides which target proteins to the plastids such as that of rapeseed enoyl-Acp reductase (Verwaert et al. (1994) *Plant Mol. Biol.* 26:189–202) are useful in the invention.

Methods for introducing nucleotide constructs into animal cells are known in the art including, but not limited to, stable transformation methods, transient transformation methods, and virus-mediated methods. Transformation protocols as well as protocols for introducing nucleotide sequences into animal cells may vary depending on whether in vitro or in vivo expression is desired. Suitable methods of introducing nucleotide sequences into animal cells and subsequent insertion into the animal genome include transformation of embryonic stem cells or primordial germ cells in tissue culture with a subsequent injection of transformed cells into the inner cell mass of blastocytes, which are then implanted into the uterus of a hormonally induced (pseudopregnant) animal (see U.S. Pat. No. 6,271,436, herein incorporated by reference), injection of the expression cassette directly into a fertilized egg, which is subsequently implanted in the uterus of a receptive, pseudopregnant animal (see Wall et al. (1985) *Biol. Reprod.* 32:645–651; Hammer, et al. (1985) *Nature* 315:680–683; Angelika, et al. (1997) *Science* 278:2130–2133; herein incorporated by reference), transformation of differentiated cells in tissue culture, such as fibroblasts, with the nucleotide sequence of interest, and fusion of the transformed cells with enucleated oocytes or microinjection of transformed fibroblasts into mature oocytes (Kuhholzer et al. (2000) *Mol Reprod Dev* 56:145–148 and Tao et al. (1999) *Anim Reprod Sci* 56:133–141 herein incorporated by reference), and transformation of sperm cells and in vitro fertilization with the transformed sperm cells. For a discussion of gene expression in animals see Old et al (1989) "Principles of Gene Manipulation," Blackwell Scientific Publications, London.

The offspring of females implanted with transformed eggs will be tested for the presence of the desired gene by removing a small piece of tissue, extracting DNA and assaying it for the presence of the gene by methods known to those skilled in the art including, but not limited to, PCR and Southern hybridization. The positive F1 animals will be tested for the expression of the nucleotide sequence of interest in target tissue by methods known to one skilled in the art including, but not limited to, RT-PCR and Northern hybridization. The F1 animals that express the nucleotide sequences of the invention are tested for zearalenone detoxification activity using assay techniques known to one skilled in the art including, but not limited to, monitoring degradation of zearalenone substrates after incubation with protein extracts from the F1 animals using HPLC or ELISAs and toxicity assays such as feeding.

Once transgenic animals expressing the gene are produced, they can be propagated by sexual reproduction or cloning without the need of repeated transformations. In one embodiment of the invention, transgenic animals produce zearalenone detoxifying enzymes in their digestive tract. In another embodiment, a composition of the invention is the saliva or bodily fluids secreted to the digestive tract of the animal having zearalenone detoxifying activity.

Prokaryotic cells may be used as hosts for expression. Prokaryotes most frequently are represented by various strains of *E. coli*; however, other microbial strains may also be used. Commonly used prokaryotic control sequences which are defined herein to include promoters for transcription initiation, optionally with an operator, along with ribosome binding sequences, include such commonly used promoters as the beta lactamase (penicillinase) and lactose (lac) promoter systems (Chang et al. (1977) *Nature* 198:1056), the tryptophan (trp) promoter system (Goeddel et al. (1980) *Nucleic Acids Res.* 8:4057) and the lambda derived P L promoter and N-gene ribosome binding site (Shimatake et al. (1981) *Nature* 292:128). Examples of selection markers for *E. coli* and other microbial organisms include, for example, genes specifying resistance to ampicillin, tetracycline, or chloramphenicol.

The vector is selected to allow introduction into the appropriate host cell. Bacterial vectors are typically of plasmid or phage origin. Appropriate bacterial cells are infected with phage vector particles or transfected with naked phage vector DNA. If a plasmid vector is used, the bacterial cells are transfected with the plasmid vector DNA. Expression systems for expressing a protein of the present invention are available using Bacillus sp. and Salmonella (Palva et al. (1983) *Gene* 22:229–235 and Mosbach et al. (1983) *Nature* 302:543–545).

A variety of eukaryotic expression systems such as yeast, insect cell lines, plant and mammalian cells, are known to those of skill in the art. As explained briefly below, a polynucleotide of the present invention can be expressed in these eukaryotic systems. In some embodiments, transformed/transfected plant cells, as discussed infra, are employed as expression systems for production of the proteins of the instant invention.

Synthesis of heterologous nucleotide sequences in yeast is well known. Sherman, F., et al. (1982) *Methods in Yeast Genetics*, Cold Spring Harbor Laboratory is a well recognized work describing the various methods available to produce the protein in yeast. Two widely utilized yeasts for production of eukaryotic proteins are *Saccharomyces cerevisiae* and *Pichia pastoris*. Vectors, strains, and protocols for expression in Saccharomyces and Pichia are known in the art and available from commercial suppliers (e.g., Invitrogen). Suitable vectors usually have expression control sequences, such as promoters, including 3-phosphoglycerate kinase or alcohol oxidase, and an origin of replication, termination sequences and the like as desired.

A protein of the present invention, once expressed, can be isolated from yeast by lysing the cells and applying standard protein isolation techniques to the lysates. The monitoring of the purification process can be accomplished by using Western blot techniques or radioimmunoassay of other standard immunoassay techniques.

The sequences of the present invention can also be ligated to various expression vectors for use in transfecting cell cultures of, for instance, mammalian, insect, or plant origin. A number of suitable host cell lines capable of expressing intact proteins have been developed in the art, and include the HEK293, BHK21, and CHO cell lines. Expression vectors for these cells can include expression control sequences, such as an origin of replication, a promoter (e.g. the CMV promoter, a HSV tk promoter or pgk (phosphoglycerate kinase) promoter), an enhancer (Queen et al. (1986) *Immunol. Rev.* 89:49), and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection.

Appropriate vectors for expressing proteins of the present invention in insect cells are usually derived from the SF9 baculovirus. Suitable insect cell lines include mosquito larvae, silkworm, armyworm, moth and Drosophila cell lines such as a Schneider cell line (See, Schneider, J. *Embryol. Exp. Morphol.* 27:353–365 (1987).

As with yeast, when higher animal or plant host cells are employed, polyadenylation or transcription terminator sequences are typically incorporated into the vector. An example of a terminator sequence is the polyadenylation sequence from the bovine growth hormone gene. Sequences for accurate splicing of the transcript may also be included. An example of a splicing sequence is the VP1 intron from SV40 (Sprague, et al.(1983) *J. Virol.* 45:773–781). Additionally, gene sequences to control replication in the host cell may be incorporated into the vector such as those found in bovine papilloma virus type-vectors. Saveria-Campo, M., (1985) Bovine Papilloma Virus DNA a Eukaryotic Cloning Vector in DNA Cloning Vol. II a Practical Approach, D. M. Glover, Ed., IRL Press, Arlington, Va. pp. 213–238.

Animal and lower eukaryotic (e.g., yeast) host cells are competent or rendered competent for transfection by various means. There are several well-known methods of introducing DNA into animal cells. These include: calcium phosphate precipitation, fusion of the recipient cells with bacterial protoplasts containing the DNA, treatment of the recipient cells with liposomes containing the DNA, DEAE dextrin, electroporation, biolistics, and micro-injection of the DNA directly into the cells. The transfected cells are cultured by means well known in the art. Kuchler, R. J. (1997) *Biochemical Methods in Cell Culture and Virology*, Dowden, Hutchinson and Ross, Inc.

As discussed elsewhere herein, the ZES1, ZES2, and ZES2b sequences of the invention have sequence similarity to known esterases and are upregulated in the presence of zearalenone and α-zearalenol. Hence, the sequences may find use in detoxifying a mycotoxin. By "mycotoxin detoxification compositions" is intended a composition that is capable of detoxifying mycotoxins, particularly zearalenone. A mycotoxin detoxification composition reduces the toxicity of the mycotoxin by at least about 5% to about 50%, at least about 10% to about 60%, at least about 30% to about 70%, at least about 40% to about 80%, or at least about 50% to about 90% or greater. Hence, the methods of the invention can be utilized to protect animals from disease, particularly those diseases that are caused by fungal toxins found upon or in plants. Mycotoxin detoxification compositions of the invention include, for example, the sequences set forth in SEQ ID NOS:1, 3, and 5, compositions comprising the polypeptides encoded by these sequences (SEQ ID NOS:2, 4, 6, and 7), and microbes and plants expressing the sequences of the invention.

Methods for assaying mycotoxin detoxification are known in the art. For example, a plant either expressing a mycotoxin detoxification polypeptide or having a mycotoxin detoxification composition applied to its surface shows a decrease in mycotoxin levels following mycotoxin challenge when compared to a control plant that was not exposed to the mycotoxin detoxification composition. In another type of assay, the consumer of a plant either expressing a mycotoxin detoxification polypeptide or having a mycotoxin detoxification composition applied to its surface exhibits less reaction to the mycotoxin than the consumer of a control plant. As another example, a plant expressing a mycotoxin detoxification polypeptide or exposed to a mycotoxin detoxification composition is challenged with mycotoxin producing fungus. A control sample does not express or is not exposed to a mycotoxin detoxification composition. The plants are extracted in a suitable organic solvent or organic aqueous mixture for recovering said mycotoxin. The resulting extract is then concentrated and subjected to HPLC analysis to determine the amounts of said mycotoxin. The amount of the mycotoxin detected in the extract is compared to the amount of the mycotoxin in the control sample, and the efficacy of removal of the mycotoxin is expressed as a percent reduction in the level of the mycotoxin in the experimental extract as compared to the level of the mycotoxin in the control sample. In the present invention, said mycotoxin is preferably zearalenone or a structurally related analog thereof.

Methods to assay for the detoxification of zearalenone and structurally related analogs are known in the art. Zearalenone detoxification can be evaluated by techniques comprising crystal disappearance assays, thin layer chromatography, ELISA, and mouse uterine weight assays. See, for example, Megharaj et al. (1997) *Lett. Appl. Micro.* 24:329–333, and U.S. Pat. Nos. 5,962,304 and 6,074,838, herein incorporated by reference. Organisms that have stably incorporated the nucleotide sequences of the invention can be grown on media containing radioactively labeled zearalenone, the label traced, and the degraded toxin isolated for further study. The degraded zearalenone can be compared to the active compound for its mammalian toxicity in known sensitive species, such as porcines and bovines. Such toxicity assays are known in the art. For example, the mouse uterine weight bioassay can be used to compare toxicity (Lemke et al. (1999) *J. Toxicol Environ Health.* 56:283–295). For purposes of the invention, the zearalenone or zearalenone degradation products will be degraded to at least about 50% to about 10% or less of the original toxicity, preferably about 30% to about 5% or less, more preferably about 20% to about 1% or less.

In one embodiment of the present invention, the ZES1, ZES2, and ZES2b nucleotide sequences of the invention are stably incorporated in the genome of a plant. Such transformed plants, plant cells, and seed are characterized by an enhanced ability to detoxify mycotoxins, particularly zearalenone.

In another embodiment of the present invention, the zearalenone detoxification compositions comprise a microbe having stably integrated a ZES1, ZES2, or ZES2b nucleotide sequence. The resulting microbes can be processed and used as a microbial spray. Any suitable microorganism can be used for this purpose. See, for example, Gaertner et al. (1993) in *Advanced Engineered Pesticides*, Kim (Ed.). In one embodiment, the nucleotide sequences of the invention are introduced into microorganisms that multiply on plants (epiphytes) to deliver the ZES1, ZES2, or ZES2b polypeptides to potential target crops. Epiphytes can be, for example, grain-positive or gram-negative bacteria.

In one specific embodiment of the invention, the detoxification of a mycotoxin, particularly zearalenone or a structurally related mycotoxin, upon or in a plant, upon or in grain, upon or in processed grain is achieved by applying *G. roseum* having stably incorporated the ZES1, ZES2, or ZES2b nucleotide sequences operably linked to a heterologous promoter.

It is further recognized that whole, i.e., unlysed, cells of the transformed microorganism can be treated with reagents that prolong the activity of the polypeptide produced in the microorganism when the microorganism is applied to the environment of a target plant. A secretion signal sequence may be used in combination with the gene of interest such that the resulting enzyme is secreted outside the microorganism for presentation to the target plant.

In this manner, a gene encoding a ZES1, ZES2, or ZES2b polypeptide of the invention may be introduced via a suitable vector into a microbial host, and said transformed host applied to the environment, plants, or animals. Microorganism hosts that are known to occupy the "phytosphere" (phylloplane, phyllosphere, rhizosphere, and/or rhizoplane) of one or more crops of interest may be selected for transformation. These microorganisms are selected so as to be capable of successfully competing in the particular environment with the wild-type microorganisms, to provide for stable maintenance and expression of the gene expressing the detoxifying polypeptide, and for improved protection of the enzymes of the invention from environmental degradation and inactivation.

Such microorganisms include bacteria, algae, and fungi. Of particular interest are microorganisms, such as bacteria, e.g., Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi, particularly yeast, e.g., Saccharomyces, Pichia, Cryptococcus, Kluyveromyces, Sporobolomyces, Rhodotorula, Aureobasidium, and Gliocladium. Of particular interest are such phytosphere bacterial species as *Pseudomonas syringae, Pseudomonas fluorescens, Serratia marcescens, Acetobacter xylinum,* Agrobacteria, *Rhodopseudomonas spheroides, Xanthomonas campestris, Rhizobium melioti, Alcaligenes entrophus, Clavibacter xyli,* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae,* and *Aureobasidium pullulans.*

Illustrative prokaryotes, both Gram-negative and -positive, include Enterobacteriaceae, such as Escherichia, Erwinia, Shigella, Salmonella, and Proteus; Bacillaceae; Rhizobiaceae, such as Rhizobium; Spirillaceae, such as photobacterium, Zymomonas, Serratia, Aeromonas, Vibrio, Desulfovibrio, Spirillum; Lactobacillaceae; Pseudomonadaceae, such as Pseudomonas and Acetobacter; Azotobacteraceae; and Nitrobacteraceae. Among eukaryotes are fungi, such as Phycomycetes and Ascomycetes, which includes yeast, such as Saccharomyces and Schizosaccharomyces; and Basidiomycetes yeast, such as Rhodotorula, Aureobasidium, Sporobolomyces, and the like.

In another embodiment, the zearalenone detoxifying composition comprises isolated ZES1, ZES2, and ZES2b polypeptides. The mycotoxin detoxification compositions of the invention find use in the detoxification of a mycotoxin, particularly zearalenone or a structurally related mycotoxin, during the processing of grain for animal or human food consumption; during the processing of feedstuffs, and during the processing of plant material for silage. In this embodiment, the zearalenone detoxification polypeptides of SEQ ID NO:2, SEQ ID NO:4, SEQ ID NO:6, or SEQ ID NO:7 are presented to grain, plant material for silage, or a contaminated food crop, or during appropriate stage of the processing procedure, in amounts effective for detoxification of zearalenone and structurally related mycotoxins. The compositions can be applied to the environment of a mycotoxin by, for example, spraying, atomizing, dusting, scattering, coating or pouring, introducing into or on the soil, introducing into irrigation water, by seed treatment, or dusting at the time when the source of the mycotoxin has begun to appear or before the appearance of pests as a protective measure. It is recognized that any means to bring the ZES polypeptides in contact with the mycotoxin can be used in the practice of the invention.

Methods are provided for controlling mycotoxins comprising applying a mycotoxin detoxifying amount of a polypeptide or composition of the invention to the environment of the mycotoxin. The polypeptides of the invention can be formulated with an acceptable carrier into a composition(s) that is, for example, a suspension, a solution, an emulsion, a dusting powder, a dispersible granule, a wettable powder, an emulsifiable concentrate, an aerosol, an impregnated granule, an adjuvant, a coatable paste, and also encapsulations in, for example, polymer substances.

Such compositions disclosed above may be obtained by the addition of a surface-active agent, an inert carrier, a preservative, a humectant, a feeding stimulant, an attractant, an encapsulating agent, a binder, an emulsifier, a dye, a UV protectant, a buffer, a flow agent or fertilizers, micronutrient donors or other preparations that influence plant growth. One or more agrochemicals including, but not limited to, herbicides, insecticides, fungicides, bacteriocides, nematocides, molluscicides, acaracides, plant growth regulators, harvest aids, and fertilizers, can be combined with carriers, surfactants, or adjuvants customarily employed in the art of formulation or other components to facilitate product handling and application for particular target mycotoxins. Suitable carriers and adjuvants can be solid or liquid and correspond to the substances ordinarily employed in formulation technology, e.g., natural or regenerated mineral substances, solvents, dispersants, wetting agents, tackifiers, binders, or fertilizers. The active ingredients of the present invention are normally applied in the form of compositions and can be applied to the crop area or plant to be treated, simultaneously or in succession, with other compounds. In some embodiments, methods of applying an active ingredient of the present invention or an agrochemical composition of the present invention (which contains at least one of the proteins of the present invention) are foliar application, seed coating, and soil application.

Suitable surface-active agents include, but are not limited to, anionic compounds such as a carboxylate of, for example, a metal; a carboxylate of a long chain fatty acid; an N-acylsarcosinate; mono or di-esters of phosphoric acid with fatty alcohol ethoxylates or salts of such esters; fatty alcohol sulfates such as sodium dodecyl sulfate, sodium octadecyl sulfate, or sodium cetyl sulfate; ethoxylated fatty alcohol sulfates; ethoxylated alkylphenol sulfates; lignin sulfonates; petroleum sulfonates; alkyl aryl sulfonates such as alkyl-benzene sulfonates or lower alkylnaphthalene sulfonates, e.g., butyl-naphthalene sulfonate; salts of sulfonated naphthalene-formaldehyde condensates; salts of sulfonated phenol-formaldehyde condensates; more complex sulfonates such as the amide sulfonates, e.g., the sulfonated condensation product of oleic acid and N-methyl taurine; or the dialkyl sulfosuccinates, e.g., the sodium sulfonate or dioctyl succinate. Non-ionic agents include condensation products of fatty acid esters, fatty alcohols, fatty acid amides or fatty-alkyl- or alkenyl-substituted phenols with ethylene oxide, fatty esters of polyhydric alcohol ethers, e.g., sorbitan fatty acid esters, condensation products of such esters with ethylene oxide, e.g. polyoxyethylene sorbitar fatty acid esters, block copolymers of ethylene oxide and propylene oxide, acetylenic glycols such as 2,4,7,9-tetraethyl-5-decyn-4,7-diol, or ethoxylated acetylenic glycols. Examples of a cationic surface-active agent include, for instance, an aliphatic mono-, di-, or polyamine such as an acetate, naphthenate, or oleate; or oxygen-containing amine such as an amine oxide of polyoxyethylene alkylamine; an amide-linked amine prepared by the condensation of a carboxylic acid with a di- or polyamine; or a quaternary ammonium salt.

Examples of inert materials include, but are not limited to, inorganic minerals such as kaolin, phyllosilicates, carbonates, sulfates, phosphates, or botanical materials such as cork, powdered corncobs, peanut hulls, rice hulls, and walnut shells.

The compositions of the present invention can be in a suitable form for direct application or as concentrate of primary composition, which requires dilution with a suitable quantity of water or other diluent before application. The detoxifying concentration will vary depending upon the nature of the particular formulation, specifically, whether it is a concentrate or to be used directly.

In a further embodiment, the compositions, as well as the proteins of the present invention can be treated prior to formulation to prolong the activity when applied to the environment of a mycotoxin as long as the pretreatment is not deleterious to the activity. Such treatment can be by chemical and/or physical means as long as the treatment does not deleteriously affect the properties of the composition(s). Examples of chemical reagents include, but are not limited to, halogenating agents; aldehydes such as formaldehyde and glutaraldehyde; anti-infectives, such as zephiran chloride; alcohols, such as isopropanol and ethanol; and histological fixatives, such as Bouin's fixative and Helly's fixative (see, for example, Humason (1967) Animal Tissue Techniques (W. H. Freeman and Co.).

Detoxification by this method can occur not only during the processing, but also any time prior to or during the feeding of the grain or plant material to an animal or incorporation of the grain or food crop into a human food product, or before or during ingestion of the food crop. The polypeptides or microorganisms can be applied during processing in appropriate manners, for example, as a wash or spray, or in dried or lyophilized form or powdered form, depending upon the nature of the milling process and/or the stage of processing at which the enzymatic treatment is carried out. See generally, Hoseney, R. C. (1990) *Principles of Cereal Science and Technology*, American Assn. of Cereal Chemists, Inc. (especially Chapters 5, 6 and 7); Jones, J. M. (1992) Food Safety, Eagan Press, St. Paul, Minn. (especially Chapters 7 and 9); and Jelen, P. (1985) *Introduction to Food Processing*, Restan Publ. Co., Reston, Va. Processed grain or silage to be used for animal feed or feedstuffs can be treated with an effective amount of the polypeptides in the form of an inoculant or probiotic additive, for example, or in any form recognized by those skilled in the art for use in animal feed.

In another embodiment, ruminal microorganisms can be genetically engineered to contain and express the zearalenone detoxification enzymes of the invention. The genetic engineering of microorganisms is now an art-recognized technique, and ruminal microorganisms so engineered can be added to feed in any art-recognized manner. In addition, microorganisms, plants, or other organisms or their cultured cells in vitro capable of functioning as bioreactors can be engineered so as to be capable of mass producing the zearalenone detoxification polypeptides of G. roseum.

An embodiment of the invention is a method by which the nucleotide sequences of the invention are used produce transgenic non-human animal cells or transgenic nonhuman animals expressing the polypeptides encoded by the nucleotide sequences of the invention. Transgenic non-human animals produced by the method of the invention express a polypeptide having zearalenone-detoxifying activity. The zearalenone-detoxifying activity may be expressed at levels sufficient to improve the transgenic animal's tolerance to zearalenone and related macrocyclic lactones consumed with contaminated feeds. The nucleotide sequences of the invention will be preferentially expressed by cells of digestive tract origin including, but not limited to, salivary gland cells, liver cells, and gall bladder cells.

For expression in cells of digestive tract origin, the nucleotide sequences of the invention will be operably linked with regulatory sequences enabling expression of the nucleotide sequence in animal cells, such as, but not limited to, the parotid secretory protein promoter and the metallothionein promoter (see Golovan et al. (2001) *Nature Biotechnol* 19:429–433 and Palmiter et al. (1983) *Science* 222:809–814, herein incorporated by reference). The parotid secretory protein promoter is a salivary gland-preferred promoter and allows preferential expression and secretion into the saliva, and the metallothionein promoter is a liver-preferred promoter and allows expression in the liver. Additional promoters and regulatory elements suitable for use in non-human animal cells can be found in U.S. Pat. No. 6,271,436, herein incorporated by reference. The nucleotide sequences of the invention may be operably linked to secretory signal sequences functional in non-human animal cells. The expression cassette comprising the nucleotide sequences of the invention may further comprise secretory signal sequences operably linked to the nucleotide sequences of the invention. Appropriate secretory signal sequences are known to one of skill in the art and include, but are not limited to, the secretory signals of cystatin S and Muc5B (see e.g. Cox et al. (1992) *Gene* 110:175–180 and Offner et al. (1998) *Biochem Biophys Res Commun* 251:350–355).

The expression vector may be transformed into animal cells using any method known.

This invention can be better understood by reference to the following non-limited examples. It will be appreciated by those skilled in the art that other embodiments of the invention may be practiced without departing from the spirit and the scope of the invention as herein disclosed.

EXPERIMENTAL

EXAMPLE 1
Isolation of ZES1, ZES2, and ZES2b Sequences

Synthesis of zearalenone esterase in G. roseum occurs only when zearalenone or its derivative α-zearalenol is present in the culture medium. β-zearalenol, although chemically similar to α-zearalenol, does not induce synthesis of zearalenone esterase. See, for example, Volkl et al. (1997) Mykotoxin-Workshop, Munich, Germany, 2–4 Juni 1997. Ludwig-Maximilians-Universitaet Munich, Proceedings p. 45–49; Woerfel & Karlovsky, (1998) Mykotoxin-Workshop, Detmold, Germany, 8.-10.06.1998. Institut fur Biochemie von Getreide und Kartoffeln der Bundesanstalt fur Getreide-, Kartoffel-, und Fettforshung, Proceedings p. 189–192; Woerfel, (1999) Ph.D. Dissertation Universitat Hohenheim, Stuttgart; and Karlovsky (1999) *Nat. Toxins* 7:1–23, all of which are herein incorporated by reference.

The ZES1, ZES2, and ZES2b sequences of the invention were identified by assaying for differential expression patterns in the presence of α-zearalenol and β-zearalenol, which allowed for identification of the nucleotide sequences of the invention. Specifically, G. roseum was cultured in the presence of either 10 µg/ml α-zearalenol or 10 µg/ml β-zearalenol for 12 hours at 22° C. Following culturing, Curagen Profiling technology was used to identify transcripts present in α-zearalenol-induced cultures but absent in β-zearalenol-induced cultures. The ZES1, ZES2, and ZES2b transcripts (SEQ ID NO:1, SEQ ID NO:3, and SEQ ID NO:5 respectively) were upregulated in the α-zearalenol induced cultures.

The amino acid sequences encoded by the nucleotide sequences of the invention were compared with other known amino acid sequences using a Clustal type alignment program. The ZES1, ZES2, and ZES2b genes share sequence identity with a number of known proteins, particularly esterases. ZES1 has 35% identity to a putative hydrolase from *Streptomyces coelicolor* (GenBank Accession No. CAB56657.1), 16% identity to 4-carboxymuconolactone decarboxylase homolog from *S. coelicolor* (GenBank Accession No. T29425), 23% identity to tetranactin resistance protein from *S. griseus* (GenBank Accession No. AAD37454.1), 16% identity to 3-oxoadipate enol-lactone hydrolase/4-carboxymuconolactone decarboxylase from *Rhodococcus opacus* (GenBank Accession No. AAC38246.1), and 24% identity to macrotetrolide resistance protein from *S. griseus* (GenBank Accession No. JH0655).

ZES2 has 21% identity to chloride peroxidase from *Deinococcus radiodurans* (GenBank Accession No. B75474), 14% identity to 4-carboxymuconolactone decarboxylase homolog from *S. coelicolor* (GenBank Accession No. T29425), 22% identity to 2-hydroxy-6-oxo-6-phenylhexa-2,4-dienoate hydrolase from *Burkholderia cepacia* (GenBank Accession No. P47229), 21% identity to hydrolase from *Bacillus halodurans* (GenBank Accession No. BAB07524.1), and 17% identity to lactone-specific esterase from *Pseudomonas fluorescens* (GenBank Accession No. AAC36352. 1).

EXAMPLE 2
Pichia Expression of ZES1, ZES2, and ZES2b

For cloning into *Pichia pastoris* expression vectors, oligonucleotide primers are designed that contain a 22 bp overlap of the 5' end (sense strand) and 3' end (antisense strand), respectively of the open reading frame of the ZES1, ZES2, or ZES2b nucleotide of interest, including the stop codon. In addition, each oligonucleotide has a 5' extension with digestible restriction sites that allows cloning of the amplified insert in-frame into the expression vector. pPicZalphaA is an *E. coli* compatible Pichia expression vector containing a functional yeast alpha-factor secretion signal and peptide processing sites, allowing high efficiency, inducible secretion into the culture medium of Pichia. After the generation of the 5' and 3' RACE products, the resulting band is cloned into a restriction enzyme digested pPicZalphaA plasmid.

Pichia is transformed as described in Invitrogen Manual, Easy Select™ Pichia Expression Kit, Version B, #161219, with the ZES1, ZES2, or ZES2b polynucleotides with either an intron (negative control, no expression) or without an intron (capable of making an active protein). The Pichia culture fluids and pellets are assayed for enzyme activity as described elsewhere herein.

EXAMPLE 3
Expression of ZES1, ZES2, or ZES2b in *E. coli*

A vector for expressing ZES1, ZES2, ZES2b polypeptides in *E. coli* is a prokaryotic glutathione S-transferase (GST) fusion vector for inducible, high-level intracellular expression of genes or gene fragments as fusions with *Schistosoma japonicum* GST. GST gene fusion vectors include the following features: a lac promoter for inducible, high-level expression; an internal lac Iq gene for use in any *E. coli* host; and the thrombin factor Xa or PreScission Protease recognition sites for cleaving the desired protein from the fusion product. The insert of interest is cloned into the 5' EcoRI site and a 3' NotI site allowing in-frame expression of the fusion peptide. The generation of such an insert is described in the previous example.

*E. coli* is transformed with the vector containing the coding sequence for the degradative enzyme as described in BRL catalogue, Life Technologies, Inc., catalogue; Hanahan (1983) *J. Mol. Biol.* 166:557; Jessee et al. (1984) *J. Focus* 6:4; King et al. (1986) *Focus* 8:1, and hereby incorporated by reference. The transformed *E. coli* is induced by addition of IPTG (isopropyl b-D-thiogalactopyranoside). Samples of soluble extract and samples of insoluble inclusion bodies are tested for enzyme activity as described elsewhere herein.

EXAMPLE 4
Transformation and Regeneration of Transgenic Plants

Immature maize embryos from greenhouse donor plants are bombarded with a plasmid containing the ZES1, ZES2, or ZES2b gene operably linked to a ubiquitin promoter and the selectable marker gene PAT (Wohlleben et al. (1988) *Gene* 70:25–37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising the ZES1, ZES2, or ZES2b gene operably linked to a ubiquitin promoter is made. This plasmid DNA plus plasmid DNA containing a PAT selectable marker is precipitated onto 1.1 μm (average diameter) tungsten pellets using a $CaCl_2$ precipitation procedure as follows:

100 μl prepared tungsten particles in water
10 μl (1 μg) DNA in Tris EDTA buffer (1 μg total DNA)
100 μl 2.5 M $CaCl_2$
10 μl 0.1 M spermidine Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity. Plants are monitored and scored for zearalenone esterase activity as described elsewhere herein.

Bombardment and Culture Media

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000× SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite (added after bringing to volume with D-I $H_2O$); and 0.85 mg/l silver nitrate and 3.0 mg/l bialaphos(both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l bacto-agar (added after bringing to volume with polished D-I $H_2O$), sterilized and cooled to 60° C.

EXAMPLE 5
Agrobacterium-mediated Transformation

For Agrobacterium-mediated transformation of maize with zearalenone esterase genes or nucleotide sequences of the invention, preferably the method of Zhao is employed (U.S. Pat. No. 5,981,840, and PCT patent publication WO98/32326; the contents of which are hereby incorporated by reference). Briefly, immature embryos are isolated from maize and the embryos contacted with a suspension of Agrobacterium, where the bacteria are capable of transferring the ZES1, ZES2, or ZES2b gene or nucleotide sequence of interest to at least one cell of at least one of the immature embryos (step 1: the infection step). In this step the immature embryos are preferably immersed in an Agrobacterium suspension for the initiation of inoculation. The embryos are co-cultured for a time with the Agrobacterium (step 2: the co-cultivation step). Preferably the immature embryos are cultured on solid medium following the infection step. Following this co-cultivation period an optional "resting" step is contemplated. In this resting step, the embryos are incubated in the presence of at least one antibiotic known to inhibit the growth of Agrobacterium without the addition of a selective agent for plant transformants (step 3: resting step). Preferably the immature embryos are cultured on solid medium with antibiotic, but without a selecting agent, for elimination of Agrobacterium and for a resting phase for the infected cells. Next, inoculated embryos are cultured on medium containing a selective agent and growing transformed callus is recovered (step 4: the selection step). Preferably, the immature embryos are cultured on solid medium with a selective agent resulting in the selective growth of transformed cells. The callus is then regenerated into plants (step 5: the regeneration step), and preferably calli grown on selective medium are cultured on solid medium to regenerate the plants.

EXAMPLE 6
Soybean Embryo Transformation

Soybean embryos are bombarded with a plasmid containing the ZES1, ZES2, or ZES2b nucleotide sequence operably linked to a SCP1 promoter as follows. To induce somatic embryos, cotyledons, 3–5 mm in length dissected from surface-sterilized, immature seeds of the soybean cultivar A2872, are cultured in the light or dark at 26° C. on an appropriate agar medium for six to ten weeks. Somatic embryos producing secondary embryos are then excised and placed into a suitable liquid medium. After repeated selection for clusters of somatic embryos that multiplied as early, globular-staged embryos, the suspensions are maintained as described below.

Soybean embryogenic suspension cultures can maintained in 35 ml liquid media on a rotary shaker, 150 rpm, at 26° C. with florescent lights on a 16:8 hour day/night schedule. Cultures are subcultured every two weeks by inoculating approximately 35 mg of tissue into 35 ml of liquid medium.

Soybean embryogenic suspension cultures may then be transformed by the method of particle gun bombardment (Klein et al. (1987) *Nature* (London) 327:70–73, U.S. Pat. No. 4,945,050). A Du Pont Biolistic PDS1000/HE instrument (helium retrofit) can be used for these transformations.

A selectable marker gene that can be used to facilitate soybean transformation is a transgene composed of the 35S promoter from Cauliflower Mosaic Virus (Odell et al. (1985) *Nature* 313:810–812), the hygromycin phosphotransferase gene from plasmid pJR225 (from *E. coli*; Gritz et al. (1983) *Gene* 25:179–188), and the 3' region of the nopaline synthase gene from the T-DNA of the Ti plasmid of *Agrobacterium tumefaciens*. The expression cassette comprising the ZES1, ZES2, or ZES2b gene operably linked to the SCP1 promoter can be isolated as a restriction fragment. This fragment can then be inserted into a unique restriction site of the vector carrying the marker gene.

To 50 $\mu$l of a 60 mg/ml 1 $\mu$m gold particle suspension is added (in order): 5 $\mu$l DNA (1 $\mu$g/$\mu$l), 20 $\mu$l spermidine (0.1 M), and 50 $\mu$l $CaCl_2$ (2.5 M). The particle preparation is then agitated for three minutes, spun in a microfuge for 10 seconds and the supernatant removed. The DNA-coated particles are then washed once in 400 $\mu$l 70% ethanol and resuspended in 40 $\mu$l of anhydrous ethanol. The DNA/particle suspension can be sonicated three times for one second each. Five microliters of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi, and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post-bombardment with fresh media containing 50 mg/ml hygromycin. This selective media can be refreshed weekly. Seven to eight weeks post-bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

EXAMPLE 7

Sunflower Meristem Tissue Transformation

Sunflower meristem tissues are transformed with an expression cassette containing ZES1, ZES2, or ZES2b operably linked to a SCP1 promoter as follows (see also European Patent Number EP 0 486233, herein incorporated by reference, and Malone-Schoneberg et al. (1994) *Plant Science* 103:199–207). Mature sunflower seed (*Helianthus annuus* L.) are dehulled using a single wheat-head thresher. Seeds are surface sterilized for 30 minutes in a 20% Clorox bleach solution with the addition of two drops of Tween 20 per 50 ml of solution. The seeds are rinsed twice with sterile distilled water.

Split embryonic axis explants are prepared by a modification of procedures described by Schrammeijer et al. (Schrammeijer et al. (1990) *Plant Cell Rep*. 9:55–60). Seeds are imbibed in distilled water for 60 minutes following the surface sterilization procedure. The cotyledons of each seed are then broken off, producing a clean fracture at the plane of the embryonic axis. Following excision of the root tip, the explants are bisected longitudinally between the primordial leaves. The two halves are placed, cut surface up, on GBA medium consisting of Murashige and Skoog mineral elements (Murashige et al. (1962) *Physiol. Plant*., 15:473–497), Shepard's vitamin additions (Shepard (1980) in *Emergent Techniques for the Genetic Improvement of Crops* (University of Minnesota Press, St. Paul, Minn.), 40 mg/l adenine sulfate, 30 g/l sucrose, 0.5 mg/l 6-benzylaminopurine (BAP), 0.25 mg/l indole-3-acetic acid (IAA), 0.1 mg/l gibberellic acid (GA3), pH 5.6, and 8 g/l Phytagar.

The explants are subjected to microprojectile bombardment prior to Agrobacterium treatment (Bidney et al. (1992) *Plant Mol. Biol.* 18:301–313). Thirty to forty explants are placed in a circle at the center of a 60×20 mm plate for this treatment. Approximately 4.7 mg of 1.8 mm tungsten microprojectiles are resuspended in 25 ml of sterile TE buffer (10 mM Tris HCl, 1 mM EDTA, pH 8.0) and 1.5 ml aliquots are used per bombardment. Each plate is bombarded twice through a 150 mm nytex screen placed 2 cm above the samples in a PDS 1000® particle acceleration device.

Disarmed *Agrobacterium tumefaciens* strain EHA105 is used in all transformation experiments. A binary plasmid vector comprising the expression cassette that contains the zearalenone esterase gene operably linked to the SCP1 promoter is introduced into Agrobacterium strain EHA105 via freeze-thawing as described by Holsters et al. (1978) *Mol. Gen. Genet*. 163:181–187. This plasmid further comprises a kanamycin selectable marker gene (i.e, nptII). Bacteria for plant transformation experiments are grown overnight (28° C. and 100 RPM continuous agitation) in liquid YEP medium (10 gm/l yeast extract, 10 gm/l Bactopeptone, and 5 gm/l NaCl, pH 7.0) with the appropriate antibiotics required for bacterial strain and binary plasmid maintenance. The suspension is used when it reaches an $OD_{600}$ of about 0.4 to 0.8. The Agrobacterium cells are pelleted and resuspended at a final $OD_{600}$ of 0.5 in an inoculation medium comprised of 12.5 mM MES pH 5.7, 1 gm/l $NH_4Cl$, and 0.3 gm/l $MgSO_4$.

Freshly bombarded explants are placed in an Agrobacterium suspension, mixed, and left undisturbed for 30 minutes. The explants are then transferred to GBA medium and co-cultivated, cut surface down, at 26° C. and 18-hour days. After three days of co-cultivation, the explants are transferred to 374B (GBA medium lacking growth regulators and a reduced sucrose level of 1%) supplemented with 250 mg/l cefotaxime and 50 mg/l kanamycin sulfate. The explants are cultured for two to five weeks on selection and then transferred to fresh 374B medium lacking kanamycin for one to two weeks of continued development. Explants with differentiating, antibiotic-resistant areas of growth that have not produced shoots suitable for excision are transferred to GBA medium containing 250 mg/l cefotaxime for a second 3-day phytohormone treatment. Leaf samples from green, kanamycin-resistant shoots are assayed for the presence of NPTII by ELISA and for the presence of transgene expression by assaying for zearalenone esterase activity as described earlier.

NPTII-positive shoots are grafted to Pioneer® hybrid 6440 in vitro-grown sunflower seedling rootstock. Surface sterilized seeds are germinated in 48-0 medium (half-strength Murashige and Skoog salts, 0.5% sucrose, 0.3% gelrite, pH 5.6) and grown under conditions described for explant culture. The upper portion of the seedling is removed, a 1 cm vertical slice is made in the hypocotyl, and the transformed shoot inserted into the cut. The entire area is wrapped with parafilm to secure the shoot. Grafted plants can be transferred to soil following one week of in vitro culture. Grafts in soil are maintained under high humidity conditions followed by a slow acclimatization to the greenhouse environment. Transformed sectors of $T_0$ plants (parental generation) maturing in the greenhouse are identified by NPTII ELISA and/or by zearalenone esterase activity analysis of leaf extracts while transgenic seeds harvested from NPTII-positive $T_0$ plants are identified by zearalenone esterase activity analysis of small portions of dry seed cotyledon.

An alternative sunflower transformation protocol allows the recovery of transgenic progeny without the use of chemical selection pressure. Seeds are dehulled and surface-sterilized for 20 minutes in a 20% Clorox bleach solution with the addition of two to three drops of Tween 20 per 100 ml of solution, then rinsed three times with distilled water. Sterilized seeds are imbibed in the dark at 26° C. for 20 hours on filter paper moistened with water. The cotyledons and root radical are removed, and the meristem explants are cultured on 374E (GBA medium consisting of MS salts, Shepard vitamins, 40 mg/l adenine sulfate, 3% sucrose, 0.5 mg/l 6-BAP, 0.25 mg/l IAA, 0.1 mg/l GA, and 0.8% Phytagar at pH 5.6) for 24 hours under the dark. The primary leaves are removed to expose the apical meristem, around 40 explants are placed with the apical dome facing upward in a 2 cm circle in the center of 374M (GBA medium with 1.2% Phytagar), and then cultured on the medium for 24 hours in the dark.

Approximately 18.8 mg of 1.8 μm tungsten particles are resuspended in 150 μl absolute ethanol. After sonication, 8 μl of it is dropped on the center of the surface of macrocarrier. Each plate is bombarded twice with 650 psi rupture discs in the first shelf at 26 mm of Hg helium gun vacuum.

The plasmid of interest is introduced into *Agrobacterium tumefaciens* strain EHA105 via freeze thawing as described previously. The pellet of overnight-grown bacteria at 28° C. in a liquid YEP medium (10 g/l yeast extract, 10 g/l Bactopeptone, and 5 g/l NaCl, pH 7.0) in the presence of 50 μg/l kanamycin is resuspended in an inoculation medium (12.5 mM 2-mM 2-(N-morpholino) ethanesulfonic acid, MES, 1 g/l $NH_4Cl$ and 0.3 g/l $MgSO_4$ at pH 5.7) to reach a final concentration of 4.0 at OD 600. Particle-bombarded explants are transferred to GBA medium (374E), and a droplet of bacteria suspension is placed directly onto the top of the meristem. The explants are co-cultivated on the medium for 4 days, after which the explants are transferred to 374C medium (GBA with 1% sucrose and no BAP, IAA, GA3 and supplemented with 250 μg/ml cefotaxime). The plantlets are cultured on the medium for about two weeks under 16-hour day and 26° C. incubation conditions.

Explants (around 2 cm long) from two weeks of culture in 374C medium are screened for zearalenone detoxification activity using assays known in the art (El-Sharkawy et al. (1988) *Xenobiotica* 18:365–371) and as described elsewhere herein. After positive (i.e., for zearalenone esterase expression) explants are identified, those shoots that fail to exhibit zearalenone esterase activity are discarded, and every positive explant is subdivided into nodal explants. One nodal explant contains at least one potential node. The nodal segments are cultured on GBA medium for three to four days to promote the formation of auxiliary buds from each node. Then they are transferred to 374C medium and allowed to develop for an additional four weeks. Developing buds are separated and cultured for an additional four weeks on 374C medium. Pooled leaf samples from each newly recovered shoot are screened again by the appropriate protein activity assay. At this time, the positive shoots recovered from a single node will generally have been enriched in the transgenic sector detected in the initial assay prior to nodal culture.

Recovered shoots positive for zearalenone esterase expression are grafted to Pioneer hybrid 6440 in vitro-grown sunflower seedling rootstock. The rootstocks are prepared in the following manner. Seeds are dehulled and surface-sterilized for 20 minutes in a 20% Clorox bleach solution with the addition of two to three drops of Tween 20 per 100 ml of solution, and are rinsed three times with distilled water. The sterilized seeds are germinated on the filter moistened with water for three days, then they are transferred into 48 medium (half-strength MS salt, 0.5% sucrose, 0.3% gelrite pH 5.0) and grown at 26° C. under the dark for three days, then incubated at 16-hour-day culture conditions. The upper portion of selected seedling is removed, a vertical slice is made in each hypocotyl, and a transformed shoot is inserted into a V-cut. The cut area is wrapped with parafilm. After one week of culture on the medium, grafted plants are transferred to soil. In the first two weeks, they are maintained under high humidity conditions to acclimatize to a greenhouse environment.

EXAMPLE 6

In vitro Transcription and Translation of ZES2b

Cloning of the ZES2b gene into a vector suitable for in vitro transcription and translation was accomplished using methods available to one skilled in the art. The ZES2b (SEQ ID NO:5) sequence was amplified from both cDNA and genomic DNA using the oligonucleotide primers set forth in SEQ ID NOS:8 and 9. The primer in SEQ ID NO:9 altered the ZES2b termination codon from UGA to UAA to improve translation termination in the system. The primer set forth in SEQ ID NO:8 introduced a NdeI restriction site, while the primer set forth in SEQ ID NO:9 introduced a SmaI restriction site. The amplification products were resolved by gel electrophoresis and the desired amplification product was purified. The amplification products and an expression vector designed for coupled in vitro transcription and translation were incubated with the NdeI and SmaI restriction enzymes using the manufacturer's recommended conditions. The expression vector is designed for use in the RTS500 Cell-free Expression System and Rapid Translation System (available from Roche, cat. No. 3,018,008). The amplification products were ligated into the digested expression vector, using standard methods. The expression vector containing the amplification product from the cDNA was designated pFMB35-34, and the expression vector containing the amplification product from the genomic DNA was designated pFMB35-13. The sequence of the ZES2b insert in the expression constructs was confirmed by sequencing.

12 μg of each plasmid were used as a template for coupled transcription/translation reactions. The Roche system allows simultaneous transcription by T7 polymerase and translation by E. coli ribosomes. The transcription/translation reactions were performed in 1 ml reaction volumes. The plasmid DNA was incubated with the components of the transcription/translation system for 19 hours at 30° C.

EXAMPLE 7

Assay of Activity of ZES2b Translation Products

Reaction mixtures containing 100 μl of zearalenone, α-zearalenol, or β-zearalenol at 10 μg/ml in 50 mM Tris pH 8.0 were prepared. 100 μl of the pFMB35-13 or pFMB-34 translation products were added to the reaction mixtures. The reaction mixtures were incubated at 37° C. for 16 hours. After incubation, the reactions were extracted twice with 200 μl ethyl acetate. The extracts were dried in vacuo, and the residues were dissolved in 600 μl of 50% methanol.

The dissolved residues were analyzed by HPLC to determine the amount of substrate remaining. An Agilent 1100 HPLC system with a Waters Nova-Pak C18, 60A, 4 μm, 3.9×150 mm column was used to analyze the residue. The HPLC was performed at 25° C. using isocratic elution with a flow rate of 0.6 ml/min. The mobile phase was 54:36:10 methanol:water:acetonitrile. 20 μl of sample was injected onto the column and the absorption at 236 nm was measured. Under these conditions, zearalenone is retained on the column for 7.9 minutes, α-zearalenol is retained for 6.5 minutes, and β-zearalenol is retained for 4.7 minutes.

After incubation with the translation product of either pFMB35-13 or pFMB35-34, all three substrates (zearalenone, α-zearalenol, and β-zearalenol) were completely degraded. In each reaction a new peak with a retention time of 1.97 min appeared. The UV spectrum of the new peak was determined to have a maximum at 260 nm. The retention time and the UV spectrum were consistent with the properties of the hydrolysis products of the substrates.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiments.

What is claimed is:

1. An isolated nucleic acid molecule having a nucleotide sequence selected from the group consisting of:
   a) the nucleotide sequence set forth in SEQ ID NO: 5;
   b) a nucleotide sequence having at least 95% sequence identity to SEQ ID NO: 5, wherein said nucleotide sequence encodes a polypeptide having zearalenone detoxification activity; and
   c) a nucleotide sequence encoding the amino acid sequence of SEQ ID NO: 6.

2. An expression cassette comprising the nucleotide sequence of claim 1, wherein said nucleotide sequence is operably linked to a promoter.

3. The expression cassette of claim 2, wherein said promoter is a constitutive promoter.

4. The expression cassette of claim 2, wherein said promoter is active in a plant cell.

5. An expression vector comprising the expression cassette of claim 2.

6. A host cell having stably incorporated in its genome the expression cassette of claim 2.

7. A plant cell having stably incorporated in its genome a nucleotide sequence operably linked to a promoter active in said cell, wherein said nucleotide sequence is selected from the group consisting of:
   a) the nucleotide sequence set forth in SEQ ID NO: 5;
   b) a nucleotide sequence having at least 95% sequence identity to SEQ ID NO: 5, wherein said nucleotide sequence encodes a polypeptide having zearalenone detoxification activity; and
   c) a nucleotide sequence encoding the amino acid sequence of SEQ ID NO: 6.

8. The plant cell of claim 7, wherein said plant cell is from a monocotylodonous plant.

9. The plant cell of claim 7, wherein said plant cell is from a dicotyledonous plant.

10. A plant having stably incorporated in its genome a nucleotide sequence operably linked to a promoter active in said plant, wherein said nucleotide sequence is selected from the group consisting of:
    a) the nucleotide sequence set forth in SEQ ID NO: 5;
    b) a nucleotide sequence having at least 95% sequence identity to SEQ ID NO: 5, wherein said nucleotide sequence encodes a polypeptide having zearalenone detoxification activity; and
    c) a nucleotide sequence encoding the amino acid sequence of SEQ ID NO: 6.

11. The plant of claim 10, wherein said plant is a monocotyledonous plant.

12. The plant of claim 10, wherein said plant is a dicotyledonous plant.

13. A transformed seed of the plant of claim 10.

14. A method for detoxifying zearlenone in a plant, said method comprising stably incorporating into a plant a nucleotide sequence operably linked to a promoter active in said plant, wherein said nucleotide sequence is selected from the group consisting of:
    a) the nucleotide sequence set forth in SEQ ID NO: 5;
    b) a nucleotide sequence having at least 95% sequence identity to SEQ ID NO: 5, wherein said nucleotide sequence encodes a polypeptide having zearalenone detoxification activity; and
    c) a nucleotide sequence encoding the amino acid sequence of SEQ ID NO: 6.

15. The method of claim 14, wherein said plant is a monocotyledonous plant.

16. The method of claim 14, wherein said plant is a dicotyledonous plant.

17. The method of claim 14, said plant is a crop plant selected from the group consisting of maize, wheat, sorghum, rice, barley, soybean, alfalfa, sunflower, Brassica, and tomato.

18. An isolated nucleic acid molecule comprising a nucleotide sequence encoding a polypeptide having at least 95% sequence identity to the amino acid sequence set forth in SEQ ID NO:6, wherein said polypeptide has zearalenone detoxification activity.

19. An expression cassette comprising the nucleotide sequence of claim 18, wherein said nucleotide sequence is operably linked to a promoter.

20. A plant cell having stably incorporated in its genome a nucleotide sequence operably linked to a promoter active in said coil, wherein said nucleotide sequence encodes a polypeptide having at least 95% sequence identity to the amino acid sequence set forth in SEQ ID NO:6, wherein said polypeptide has zearalenone detoxification activity.

21. A plant having stably incorporated in its genome a nucleotide sequence operably linked to a promoter active in said plant, wherein said nucleotide sequence encodes a polypeptide having at least 95% sequence identity to the amino acid sequence set forth in SEQ ID NO:6, wherein said polypeptide has zearalenone detoxification activity.

* * * * *

UNITED STATES PATENT AND TRADEMARK OFFICE
CERTIFICATE OF CORRECTION

PATENT NO. : 6,812,380 B2
DATED : November 2, 2004
INVENTOR(S) : Karlovsky et al.

It is certified that error appears in the above-identified patent and that said Letters Patent is hereby corrected as shown below:

Column 49,
Line 52, "monocotylodonous" should read -- monocotyledonous --;

Column 50,
Line 41, insert -- wherein -- after "claim 14,";
Line 55, "coil" should read -- cell --.

Signed and Sealed this

Nineteenth Day of April, 2005

JON W. DUDAS
*Director of the United States Patent and Trademark Office*

SEQUENCE LISTING

<160> NUMBER OF SEQ ID NOS: 9

<210> SEQ ID NO 1
<211> LENGTH: 807
<212> TYPE: DNA
<213> ORGANISM: Gliocladium roseum
<220> FEATURE:
<221> NAME/KEY: CDS
<222> LOCATION: (1)...(807)

<400> SEQUENCE: 1

```
atg gca att acc tac att gag acc gac ggc ggc aag ctt gcc gta gaa        48
Met Ala Ile Thr Tyr Ile Glu Thr Asp Gly Gly Lys Leu Ala Val Glu
 1               5                  10                  15
```

-continued

```
gtt gag ggc gag ggt ccg ctt gtc atc tgc tcg cct ggc atg ggc gac      96
Val Glu Gly Glu Gly Pro Leu Val Ile Cys Ser Pro Gly Met Gly Asp
            20                  25                  30 acc cga gaa gcc tac gcc ccg atg gct gct cag ctc gtg gcc gcc ggc     144
Thr Arg Glu Ala Tyr Ala Pro Met Ala Ala Gln Leu Val Ala Ala Gly
        35                  40                  45 tac cgc gtg gcc cgc gtc gat ctg cgt gga cac ggc gac agc acc gca     192
Tyr Arg Val Ala Arg Val Asp Leu Arg Gly His Gly Asp Ser Thr Ala
    50                  55                  60 aac ttc aac cgc tac ggc gac gaa gcg acc gcc gac gac tac ctt aca     240
Asn Phe Asn Arg Tyr Gly Asp Glu Ala Thr Ala Asp Asp Tyr Leu Thr
65                  70                  75                  80 att att caa aca ctg ggc gca gac cgc gcc gtc ctg gca ggt gcc tcg     288
Ile Ile Gln Thr Leu Gly Ala Asp Arg Ala Val Leu Ala Gly Ala Ser
                85                  90                  95 atg tcg gct gcc gcg gct tac att gcg gca gga aaa caa ccc gac aag     336
Met Ser Ala Ala Ala Ala Tyr Ile Ala Ala Gly Lys Gln Pro Asp Lys
            100                 105                 110 atc gcc ggc ctg gtc tta att gga gcc ttt ctc cgc aac ggt ggg agc     384
Ile Ala Gly Leu Val Leu Ile Gly Ala Phe Leu Arg Asn Gly Gly Ser
        115                 120                 125 aag atg atg ctc tac gtc tta cgt atg gca ctc cta cag cct tgg ggg     432
Lys Met Met Leu Tyr Val Leu Arg Met Ala Leu Leu Gln Pro Trp Gly
    130                 135                 140 ccc act gta tgg cgc agt tat gcc tct ggc ctc tgg cct gga ctt ggc     480
Pro Thr Val Trp Arg Ser Tyr Ala Ser Gly Leu Trp Pro Gly Leu Gly
145                 150                 155                 160 gag aag gcg gct gcc gag cgc gcg gcc gcg aca act gca atg ctg acg     528
Glu Lys Ala Ala Ala Glu Arg Ala Ala Ala Thr Thr Ala Met Leu Thr
                165                 170                 175 cga ccg ggg aga tgg agc gcc ttt cgc tcc acc gtg gcc ggc tgc gac     576
Arg Pro Gly Arg Trp Ser Ala Phe Arg Ser Thr Val Ala Gly Cys Asp
            180                 185                 190 cat agt gtg gtt gag ccc tac ctt gga aag gtg aag gtg cca ggg ctg     624
His Ser Val Val Glu Pro Tyr Leu Gly Lys Val Lys Val Pro Gly Leu
        195                 200                 205 gtc gtt att ggc gac tcc gac ccg gac tgg tct cag cct ttg gag gag     672
Val Val Ile Gly Asp Ser Asp Pro Asp Trp Ser Gln Pro Leu Glu Glu
    210                 215                 220 gcc aag tgg gtt gca tcc aac ttc gaa gat gct gag act att gcc gtg     720
Ala Lys Trp Val Ala Ser Asn Phe Glu Asp Ala Glu Thr Ile Ala Val
225                 230                 235                 240 gct ggt gct ggt cac gct cct caa ttt gag aat cct gac gtt gtc gca     768
Ala Gly Ala Gly His Ala Pro Gln Phe Glu Asn Pro Asp Val Val Ala
                245                 250                 255 cca ggc gtc att tca ttc ttg agc aag cta aat ttt tag                 807
Pro Gly Val Ile Ser Phe Leu Ser Lys Leu Asn Phe *
            260                 265
```

<210> SEQ ID NO 2
<211> LENGTH: 268
<212> TYPE: PRT
<213> ORGANISM: Gliocladium roseum

<400> SEQUENCE: 2

```
Met Ala Ile Thr Tyr Ile Glu Thr Asp Gly Gly Lys Leu Ala Val
1               5                   10                  15

Val Glu Gly Glu Gly Pro Leu Val Ile Cys Ser Pro Gly Met Gly Asp
            20                  25                  30
```

```
Thr Arg Glu Ala Tyr Ala Pro Met Ala Ala Gln Leu Val Ala Ala Gly
        35                  40                  45

Tyr Arg Val Ala Arg Val Asp Leu Arg Gly His Gly Asp Ser Thr Ala
    50                  55                  60

Asn Phe Asn Arg Tyr Gly Asp Glu Ala Thr Ala Asp Asp Tyr Leu Thr
 65                  70                  75                  80

Ile Ile Gln Thr Leu Gly Ala Asp Arg Ala Val Leu Ala Gly Ala Ser
                85                  90                  95

Met Ser Ala Ala Ala Ala Tyr Ile Ala Ala Gly Lys Gln Pro Asp Lys
            100                 105                 110

Ile Ala Gly Leu Val Leu Ile Gly Ala Phe Leu Arg Asn Gly Gly Ser
        115                 120                 125

Lys Met Met Leu Tyr Val Leu Arg Met Ala Leu Leu Gln Pro Trp Gly
    130                 135                 140

Pro Thr Val Trp Arg Ser Tyr Ala Ser Gly Leu Trp Pro Gly Leu Gly
145                 150                 155                 160

Glu Lys Ala Ala Ala Glu Arg Ala Ala Ala Thr Thr Ala Met Leu Thr
                165                 170                 175

Arg Pro Gly Arg Trp Ser Ala Phe Arg Ser Thr Val Ala Gly Cys Asp
            180                 185                 190

His Ser Val Val Glu Pro Tyr Leu Gly Lys Val Lys Val Pro Gly Leu
        195                 200                 205

Val Val Ile Gly Asp Ser Asp Pro Asp Trp Ser Gln Pro Leu Glu Glu
    210                 215                 220

Ala Lys Trp Val Ala Ser Asn Phe Glu Asp Ala Glu Thr Ile Ala Val
225                 230                 235                 240

Ala Gly Ala Gly His Ala Pro Gln Phe Glu Asn Pro Asp Val Val Ala
                245                 250                 255

Pro Gly Val Ile Ser Phe Leu Ser Lys Leu Asn Phe
            260                 265

<210> SEQ ID NO 3
<211> LENGTH: 789
<212> TYPE: DNA
<213> ORGANISM: Gliocladium roseum
<220> FEATURE:
<221> NAME/KEY: CDS
<222> LOCATION: (1)...(789)

<400> SEQUENCE: 3 atg cgc att cgc agc aca atc tcg acc ccg aat ggc atc acc tgg tac    48
Met Arg Ile Arg Ser Thr Ile Ser Thr Pro Asn Gly Ile Thr Trp Tyr
 1               5                  10                  15 tat gag cag gag ggt acm gga ccc gac gtt gtc ctc gtc cct gat ggg    96
Tyr Glu Gln Glu Gly Xaa Gly Pro Asp Val Val Leu Val Pro Asp Gly
                20                  25                  30 ctc gga gaa tgc cag atg ttt gac cgc tcc gtg tcg cag att gct gct   144
Leu Gly Glu Cys Gln Met Phe Asp Arg Ser Val Ser Gln Ile Ala Ala
            35                  40                  45 caa ggc ttc agg gtc act acg ttt gat atg ccc gga atg tcc cgg tct   192
Gln Gly Phe Arg Val Thr Thr Phe Asp Met Pro Gly Met Ser Arg Ser
        50                  55                  60 gtg aag gca cca ccc gag acc tac act gag gtc acg gcc cag aag ctg   240
Val Lys Ala Pro Pro Glu Thr Tyr Thr Glu Val Thr Ala Gln Lys Leu
 65                  70                  75                  80 gct tcc tat gtc atc tcc gtc ctg gat gct ctt gac atc aag cac gct   288
Ala Ser Tyr Val Ile Ser Val Leu Asp Ala Leu Asp Ile Lys His Ala
                85                  90                  95
```

```
act gtc tgg ggc tgc agc tca gga gct tcc acc gtc gtg gcg ctg ttg    336
Thr Val Trp Gly Cys Ser Ser Gly Ala Ser Thr Val Val Ala Leu Leu
        100                 105                 110 ctc ggt tac ccc gac agg ata cgc aac gcc atg tgc cac gaa ctg cca    384
Leu Gly Tyr Pro Asp Arg Ile Arg Asn Ala Met Cys His Glu Leu Pro
            115                 120                 125 aca aag cta ctg gac cac ctt tca aac acc gct gtg ctc gaa gac gag    432
Thr Lys Leu Leu Asp His Leu Ser Asn Thr Ala Val Leu Glu Asp Glu
        130                 135                 140 gaa atc tca aag atc ctg gcc aat gta atg ttg aac gac gtg tct gga    480
Glu Ile Ser Lys Ile Leu Ala Asn Val Met Leu Asn Asp Val Ser Gly
145                 150                 155                 160 ggc tcg gag gcg tgg caa gcc atg ggg gac gag gtg cac gcg aga ctg    528
Gly Ser Glu Ala Trp Gln Ala Met Gly Asp Glu Val His Ala Arg Leu
                165                 170                 175 cac aag aac tac ccg gtt tgg gct cga gga tac cct cgc act att cct    576
His Lys Asn Tyr Pro Val Trp Ala Arg Gly Tyr Pro Arg Thr Ile Pro
            180                 185                 190 ccc tca gct ccg gtt aag gat ccg gag gct ctg cgt ggg acc gcc tgg    624
Pro Ser Ala Pro Val Lys Asp Pro Glu Ala Leu Arg Gly Thr Ala Trp
        195                 200                 205 atc agg atg ttc gac gtt tct gaa gtc cat cgc ggg cga gac aaa tgg    672
Ile Arg Met Phe Asp Val Ser Glu Val His Arg Gly Arg Asp Lys Trp
210                 215                 220 aat tca cat ttc cga gga cac aca ctt caa tta tca ggg tat ttc atc    720
Asn Ser His Phe Arg Gly His Thr Leu Gln Leu Ser Gly Tyr Phe Ile
225                 230                 235                 240 tca gga gat gca tac cgc tca cag ggg cga gac tat cta tac tgc cga    768
Ser Gly Asp Ala Tyr Arg Ser Gln Gly Arg Asp Tyr Leu Tyr Cys Arg
                245                 250                 255 gac aga tgt tca ctt tcc taa                                        789
Asp Arg Cys Ser Leu Ser *
            260

<210> SEQ ID NO 4
<211> LENGTH: 262
<212> TYPE: PRT
<213> ORGANISM: Gliocladium roseum
<220> FEATURE:
<221> NAME/KEY: VARIANT
<222> LOCATION: (1)...(262)
<223> OTHER INFORMATION: Xaa = Any Amino Acid
<221> NAME/KEY: VARIANT
<222> LOCATION: 22
<223> OTHER INFORMATION: Xaa = Any Amino Acid

<400> SEQUENCE: 4

Met Arg Ile Arg Ser Thr Ile Ser Thr Pro Asn Gly Ile Thr Trp Tyr
1               5                   10                  15

Tyr Glu Gln Glu Gly Xaa Gly Pro Asp Val Val Leu Val Pro Asp Gly
                20                  25                  30

Leu Gly Glu Cys Gln Met Phe Asp Arg Ser Val Ser Gln Ile Ala Ala
            35                  40                  45

Gln Gly Phe Arg Val Thr Thr Phe Asp Met Pro Gly Met Ser Arg Ser
        50                  55                  60

Val Lys Ala Pro Pro Glu Thr Tyr Thr Glu Val Thr Ala Gln Lys Leu
65                  70                  75                  80

Ala Ser Tyr Val Ile Ser Val Leu Asp Ala Leu Asp Ile Lys His Ala
                85                  90                  95

Thr Val Trp Gly Cys Ser Ser Gly Ala Ser Thr Val Val Ala Leu Leu
            100                 105                 110
```

```
Leu Gly Tyr Pro Asp Arg Ile Arg Asn Ala Met Cys His Glu Leu Pro
        115                 120                 125

Thr Lys Leu Leu Asp His Leu Ser Asn Thr Ala Val Leu Glu Asp Glu
130                 135                 140

Glu Ile Ser Lys Ile Leu Ala Asn Val Met Leu Asn Asp Val Ser Gly
145                 150                 155                 160

Gly Ser Glu Ala Trp Gln Ala Met Gly Asp Glu Val His Ala Arg Leu
                165                 170                 175

His Lys Asn Tyr Pro Val Trp Ala Arg Gly Tyr Pro Arg Thr Ile Pro
            180                 185                 190

Pro Ser Ala Pro Val Lys Asp Pro Glu Ala Leu Arg Gly Thr Ala Trp
        195                 200                 205

Ile Arg Met Phe Asp Val Ser Glu Val His Arg Gly Arg Asp Lys Trp
    210                 215                 220

Asn Ser His Phe Arg Gly His Thr Leu Gln Leu Ser Gly Tyr Phe Ile
225                 230                 235                 240

Ser Gly Asp Ala Tyr Arg Ser Gln Gly Arg Asp Tyr Leu Tyr Cys Arg
                245                 250                 255

Asp Arg Cys Ser Leu Ser
            260

<210> SEQ ID NO 5
<211> LENGTH: 795
<212> TYPE: DNA
<213> ORGANISM: Gliocladium roseum
<220> FEATURE:
<221> NAME/KEY: CDS
<222> LOCATION: (1)...(795)
<223> OTHER INFORMATION: Zes2b

<400> SEQUENCE: 5 atg cgc att cgc agc aca atc tcg acc ccg aat ggc atc acc tgg tac      48
Met Arg Ile Arg Ser Thr Ile Ser Thr Pro Asn Gly Ile Thr Trp Tyr
1               5                   10                  15 tat gag cag gag ggt acc gga ccc gac gtt gtc ctc gtc cct gat ggg      96
Tyr Glu Gln Glu Gly Thr Gly Pro Asp Val Val Leu Val Pro Asp Gly
            20                  25                  30 ctc gga gaa tgc cag atg ttt gac cgc tcc gtg tcg cag att gct gct     144
Leu Gly Glu Cys Gln Met Phe Asp Arg Ser Val Ser Gln Ile Ala Ala
        35                  40                  45 caa ggc ttc agg gtc act acg ttt gat atg ccc gga atg tcc cgg tct     192
Gln Gly Phe Arg Val Thr Thr Phe Asp Met Pro Gly Met Ser Arg Ser
    50                  55                  60 gtg aag gca cca ccc gag acc tac act gag gtc acg gcc cag aag ctg     240
Val Lys Ala Pro Pro Glu Thr Tyr Thr Glu Val Thr Ala Gln Lys Leu
65                  70                  75                  80 gct tcc tat gtc atc tcc gtc ctg gat gct ctt gac atc aag cac gct     288
Ala Ser Tyr Val Ile Ser Val Leu Asp Ala Leu Asp Ile Lys His Ala
                85                  90                  95 act gtc tgg ggc tgc agc tca gga gct tcc acc gtc gtg gcg ctg ttg     336
Thr Val Trp Gly Cys Ser Ser Gly Ala Ser Thr Val Val Ala Leu Leu
            100                 105                 110 ctc ggt tac ccc gac agg ata cgc aac gcc atg tgc cac gaa ctg cca     384
Leu Gly Tyr Pro Asp Arg Ile Arg Asn Ala Met Cys His Glu Leu Pro
        115                 120                 125 aca aag cta ctg gac cac ctt tca aac acc gct gtg ctc gaa gac gag     432
Thr Lys Leu Leu Asp His Leu Ser Asn Thr Ala Val Leu Glu Asp Glu
    130                 135                 140
```

```
gaa atc tca aag atc ctg gcc aat gta atg ttg aac gac gtg tct gga      480
Glu Ile Ser Lys Ile Leu Ala Asn Val Met Leu Asn Asp Val Ser Gly
145                 150                 155                 160 ggc tcg gag gcg tgg caa gcc atg ggg gac gag gtg cac gcg aga ctg      528
Gly Ser Glu Ala Trp Gln Ala Met Gly Asp Glu Val His Ala Arg Leu
                165                 170                 175 cac aag aac tac ccg gtt tgg gct cga gga tac cct cgc act att cct      576
His Lys Asn Tyr Pro Val Trp Ala Arg Gly Tyr Pro Arg Thr Ile Pro
            180                 185                 190 ccc tca gct ccg gtt aag gat ctg gag gct ctg cgt ggg aag ccc ctg      624
Pro Ser Ala Pro Val Lys Asp Leu Glu Ala Leu Arg Gly Lys Pro Leu
        195                 200                 205 gac tgg act gtc ggc gct gcg aca cca acc gag tct ttc ttt gac aac      672
Asp Trp Thr Val Gly Ala Ala Thr Pro Thr Glu Ser Phe Phe Asp Asn
    210                 215                 220 att gtt acc gct acc aag gct ggt gtc aac att ggg ttg ctt cca ggg      720
Ile Val Thr Ala Thr Lys Ala Gly Val Asn Ile Gly Leu Leu Pro Gly
225                 230                 235                 240 atg cat ttc cct tat gtt tcc cac ccg gac gtt ttc gct aaa tat gtt      768
Met His Phe Pro Tyr Val Ser His Pro Asp Val Phe Ala Lys Tyr Val
                245                 250                 255 gtg gaa act acg cag aag tat ctt tga                                  795
Val Glu Thr Thr Gln Lys Tyr Leu  *
                260
```

<210> SEQ ID NO 6
<211> LENGTH: 264
<212> TYPE: PRT
<213> ORGANISM: Gliocladium roseum

<400> SEQUENCE: 6

```
Met Arg Ile Arg Ser Thr Ile Ser Thr Pro Asn Gly Ile Thr Trp Tyr
1               5                   10                  15

Tyr Glu Gln Glu Gly Thr Gly Pro Asp Val Val Leu Val Pro Asp Gly
            20                  25                  30

Leu Gly Glu Cys Gln Met Phe Asp Arg Ser Val Ser Gln Ile Ala Ala
        35                  40                  45

Gln Gly Phe Arg Val Thr Thr Phe Asp Met Pro Gly Met Ser Arg Ser
    50                  55                  60

Val Lys Ala Pro Pro Glu Thr Tyr Thr Glu Val Thr Ala Gln Lys Leu
65                  70                  75                  80

Ala Ser Tyr Val Ile Ser Val Leu Asp Ala Leu Asp Ile Lys His Ala
                85                  90                  95

Thr Val Trp Gly Cys Ser Ser Gly Ala Ser Thr Val Val Ala Leu Leu
            100                 105                 110

Leu Gly Tyr Pro Asp Arg Ile Arg Asn Ala Met Cys His Glu Leu Pro
        115                 120                 125

Thr Lys Leu Leu Asp His Leu Ser Asn Thr Ala Val Leu Glu Asp Glu
    130                 135                 140

Glu Ile Ser Lys Ile Leu Ala Asn Val Met Leu Asn Asp Val Ser Gly
145                 150                 155                 160

Gly Ser Glu Ala Trp Gln Ala Met Gly Asp Glu Val His Ala Arg Leu
                165                 170                 175

His Lys Asn Tyr Pro Val Trp Ala Arg Gly Tyr Pro Arg Thr Ile Pro
            180                 185                 190

Pro Ser Ala Pro Val Lys Asp Leu Glu Ala Leu Arg Gly Lys Pro Leu
        195                 200                 205
```

```
Asp Trp Thr Val Gly Ala Ala Thr Pro Thr Glu Ser Phe Phe Asp Asn
    210                 215                 220

Ile Val Thr Ala Thr Lys Ala Gly Val Asn Ile Gly Leu Leu Pro Gly
225                 230                 235                 240

Met His Phe Pro Tyr Val Ser His Pro Asp Val Phe Ala Lys Tyr Val
                245                 250                 255

Val Glu Thr Thr Gln Lys Tyr Leu
                260

<210> SEQ ID NO 7
<211> LENGTH: 264
<212> TYPE: PRT
<213> ORGANISM: Gliocladium roseum

<400> SEQUENCE: 7

Met Arg Ile Arg Ser Thr Ile Ser Thr Pro Asn Gly Ile Thr Trp Tyr
  1               5                  10                  15

Tyr Glu Gln Glu Gly Thr Gly Pro Asp Val Val Leu Val Pro Asp Gly
                 20                  25                  30

Leu Gly Glu Cys Gln Met Phe Asp Arg Ser Val Ser Gln Ile Ala Ala
             35                  40                  45

Gln Gly Phe Arg Val Thr Thr Phe Asp Met Pro Gly Met Ser Arg Ser
         50                  55                  60

Val Lys Ala Pro Pro Glu Thr Tyr Thr Glu Val Thr Ala Gln Lys Leu
 65                  70                  75                  80

Ala Ser Tyr Val Ile Ser Val Leu Asp Ala Leu Asp Ile Lys His Ala
                 85                  90                  95

Thr Val Trp Gly Cys Ser Ser Gly Ala Ser Thr Val Val Ala Leu Leu
            100                 105                 110

Leu Gly Tyr Pro Asp Arg Ile Arg Asn Ala Met Cys His Glu Leu Pro
        115                 120                 125

Thr Lys Leu Leu Asp His Leu Ser Asn Thr Ala Val Leu Glu Asp Glu
    130                 135                 140

Glu Ile Ser Lys Ile Leu Ala Asn Val Met Leu Asn Asp Val Ser Gly
145                 150                 155                 160

Gly Ser Glu Ala Trp Gln Ala Met Gly Asp Glu Val His Ala Arg Leu
                165                 170                 175

His Lys Asn Tyr Pro Val Trp Ala Arg Gly Tyr Pro Arg Thr Ile Pro
            180                 185                 190

Pro Ser Ala Pro Val Lys Asp Leu Glu Ala Leu Arg Gly Lys Pro Leu
        195                 200                 205

Asp Trp Thr Val Gly Ala Ala Thr Pro Thr Glu Ser Phe Phe Asp Asn
    210                 215                 220

Ile Val Thr Ala Thr Lys Ala Gly Val Asn Ile Gly Leu Leu Pro Gly
225                 230                 235                 240

Met His Phe Pro Tyr Val Ser His Pro Asp Val Phe Ala Lys Tyr Val
                245                 250                 255

Val Glu Thr Thr Gln Lys Tyr Leu
                260

<210> SEQ ID NO 8
<211> LENGTH: 38
<212> TYPE: DNA
<213> ORGANISM: Artificial Sequence
<220> FEATURE:
<223> OTHER INFORMATION: Oligonucleotide primer with Nde1 site
```

-continued

```
<400> SEQUENCE: 8
aggagatata catatgcgca ttcgcagcac aatctcga                                38

<210> SEQ ID NO 9
<211> LENGTH: 49
<212> TYPE: DNA
<213> ORGANISM: Artificial Sequence
<220> FEATURE:
<223> OTHER INFORMATION: Oligonucleotide primer with SmaI site

<400> SEQUENCE: 9
ctggatcccg ggttaaagat acttctgcgt agtttccaca acatattta                    49
```